US011325980B2

(12) United States Patent
Sussman et al.

(10) Patent No.: US 11,325,980 B2
(45) Date of Patent: May 10, 2022

(54) COMBINATION THERAPY USING A LIV1-ADC AND A CHEMOTHERAPEUTIC

(71) Applicant: SEATTLE GENETICS, INC., Bothell, WA (US)

(72) Inventors: Django Sussman, Seattle, WA (US); Fu Li, Bothell, WA (US); Ana Kostic, Seattle, WA (US)

(73) Assignee: SEAGEN INC., Bothell, WA (US)

(*) Notice: Subject to any disclaimer, the term of this patent is extended or adjusted under 35 U.S.C. 154(b) by 226 days.

(21) Appl. No.: 16/085,511

(22) PCT Filed: Mar. 15, 2017

(86) PCT No.: PCT/US2017/022541
§ 371 (c)(1),
(2) Date: Sep. 14, 2018

(87) PCT Pub. No.: WO2017/161007
PCT Pub. Date: Sep. 21, 2017

(65) Prior Publication Data
US 2019/0085091 A1    Mar. 21, 2019

Related U.S. Application Data

(60) Provisional application No. 62/367,510, filed on Jul. 27, 2016, provisional application No. 62/317,792, filed on Apr. 4, 2016, provisional application No. 62/308,639, filed on Mar. 15, 2016.

(51) Int. Cl.
| | |
|---|---|
| *A61K 31/337* | (2006.01) |
| *A61K 31/555* | (2006.01) |
| *A61K 31/704* | (2006.01) |
| *C07K 16/30* | (2006.01) |
| *A61K 39/395* | (2006.01) |
| *A61K 47/68* | (2017.01) |
| *C07K 16/28* | (2006.01) |
| *A61K 9/00* | (2006.01) |
| *A61K 39/00* | (2006.01) |

(52) U.S. Cl.
CPC ........ *C07K 16/3015* (2013.01); *A61K 9/0019* (2013.01); *A61K 31/337* (2013.01); *A61K 31/555* (2013.01); *A61K 31/704* (2013.01); *A61K 39/39558* (2013.01); *A61K 47/6803* (2017.08); *A61K 47/6811* (2017.08); *A61K 47/6851* (2017.08); *C07K 16/28* (2013.01); *A61K 2039/505* (2013.01); *C07K 2317/24* (2013.01)

(58) Field of Classification Search
CPC ............ C07K 16/3015; A61K 47/6811; A61K 47/6851; A61K 47/6803
USPC ..................................................... 424/181.1
See application file for complete search history.

(56) References Cited

U.S. PATENT DOCUMENTS

| | | | |
|---|---|---|---|
| 4,880,935 | A | 11/1989 | Thorpe |
| 5,122,368 | A | 6/1992 | Greenfield et al. |
| 5,514,554 | A | 5/1996 | Bacus |
| 5,622,929 | A | 4/1997 | Willner et al. |
| 5,693,465 | A | 12/1997 | Manning et al. |
| 5,824,805 | A | 10/1998 | King et al. |
| 6,066,778 | A | 5/2000 | Ginsburg et al. |
| 6,130,237 | A | 10/2000 | Denny et al. |
| 6,214,345 | B1 | 4/2001 | Firestone et al. |
| 6,468,790 | B1 | 10/2002 | Giese |
| 6,762,020 | B1 | 7/2004 | Mack et al. |
| 6,884,869 | B2 | 4/2005 | Senter et al. |
| 7,022,500 | B1 | 4/2006 | Queen et al. |
| 7,091,186 | B2 | 8/2006 | Senter et al. |
| 7,098,308 | B2 | 8/2006 | Senter et al. |
| 7,141,549 | B2 | 11/2006 | Mezes et al. |
| 7,285,382 | B2 | 10/2007 | de Sauvage et al. |
| 7,288,248 | B2 | 10/2007 | Bhaskar et al. |
| 7,494,775 | B2 | 2/2009 | Veiby et al. |
| 7,498,298 | B2 | 3/2009 | Doronina et al. |
| 7,501,121 | B2 | 3/2009 | Tchistiakova et al. |
| 7,659,241 | B2 | 2/2010 | Senter et al. |
| 7,691,566 | B2 | 4/2010 | de Sauvage et al. |
| 7,705,120 | B2 | 4/2010 | Lillie et al. |
| 7,982,015 | B2 | 7/2011 | de Sauvage et al. |
| 8,313,745 | B2 | 11/2012 | Mack et al. |
| 8,323,906 | B2 | 12/2012 | Veiby et al. |
| 8,591,863 | B2 | 11/2013 | Law et al. |
| 8,642,270 | B2 | 2/2014 | Leyland-jones et al. |
| 8,728,730 | B2 | 5/2014 | Dennis, Jr. et al. |
| 8,906,342 | B2 | 12/2014 | Law et al. |
| 9,228,026 | B2 | 1/2016 | Smith et al. |
| 9,783,608 | B2 | 10/2017 | Smith et al. |
| 10,533,227 | B2 | 1/2020 | Veiby et al. |

(Continued)

FOREIGN PATENT DOCUMENTS

| | | | |
|---|---|---|---|
| CN | 1849337 | A | 10/2006 |
| CN | 101309933 | A | 11/2008 |

(Continued)

OTHER PUBLICATIONS

Slamon et al. ("Slamon", N. Engl. J. of Med, 2001 344:783-79) (Year: 2001).*

(Continued)

*Primary Examiner* — Yan Xiao
(74) *Attorney, Agent, or Firm* — Morrison & Foerster LLP

(57) ABSTRACT

The invention provides methods of treating a subject having or at risk of cancer by administering a LIV-1 antibody drug conjugate and a chemotherapeutic.

12 Claims, 8 Drawing Sheets
Specification includes a Sequence Listing.

(56) References Cited

U.S. PATENT DOCUMENTS

| | | |
|---|---|---|
| 2003/0215457 A1 | 11/2003 | de Sauvage et al. |
| 2004/0096392 A1 | 5/2004 | Bhaskar et al. |
| 2004/0141983 A1 | 7/2004 | Law et al. |
| 2004/0258616 A1 | 12/2004 | McLachlan et al. |
| 2005/0238649 A1 | 10/2005 | Doronina et al. |
| 2006/0074008 A1 | 4/2006 | Senter et al. |
| 2006/0222653 A1 | 10/2006 | Abel et al. |
| 2006/0286112 A1 | 12/2006 | Kellermann et al. |
| 2007/0264267 A1 | 11/2007 | de Sauvage et al. |
| 2008/0138345 A1 | 6/2008 | de Sauvage et al. |
| 2008/0171039 A1 | 7/2008 | Law et al. |
| 2008/0175839 A1 | 7/2008 | Law et al. |
| 2010/0158909 A1 | 6/2010 | McDonagh et al. |
| 2010/0158919 A1 | 6/2010 | Dauphin et al. |
| 2010/0196377 A1 | 8/2010 | Jantapour et al. |
| 2011/0165566 A1 | 7/2011 | Wittliff et al. |
| 2011/0166838 A1 | 7/2011 | Gehrmann et al. |
| 2011/0195995 A1 | 8/2011 | Wittliff et al. |
| 2011/0280892 A1 | 11/2011 | Kinch et al. |
| 2013/0102482 A1 | 4/2013 | Veiby et al. |
| 2013/0259860 A1 | 10/2013 | Smith et al. |
| 2014/0037540 A1 | 2/2014 | Law et al. |
| 2014/0127239 A1 | 5/2014 | Howard |
| 2016/0166665 A1 | 6/2016 | Ito et al. |
| 2016/0185858 A1 | 6/2016 | Smith et al. |
| 2018/0079810 A1 | 3/2018 | Smith et al. |
| 2020/0165335 A1 | 5/2020 | Smith |
| 2021/0228676 A1 | 7/2021 | Wang et al. |

FOREIGN PATENT DOCUMENTS

| | | |
|---|---|---|
| CN | 103533957 A | 1/2014 |
| CN | 104334189 A | 2/2015 |
| CN | 104755497 A | 7/2015 |
| CN | 104837502 A | 8/2015 |
| EP | 1263780 A2 | 12/2012 |
| EP | 3130608 A1 | 2/2017 |
| KR | 10-2005-0102627 | 10/2005 |
| WO | WO-1998/18945 A1 | 5/1998 |
| WO | WO-1998/34118 A1 | 8/1998 |
| WO | WO-1999/23230 A1 | 5/1999 |
| WO | WO-1999/25877 A1 | 5/1999 |
| WO | WO-1999/33869 A2 | 7/1999 |
| WO | WO-1999/33869 A3 | 7/1999 |
| WO | WO-2000/08210 A1 | 2/2000 |
| WO | 200055174 A1 | 9/2000 |
| WO | WO-2001/055178 A2 | 8/2001 |
| WO | WO-2001/055178 A3 | 8/2001 |
| WO | WO-2001/096372 A2 | 12/2001 |
| WO | WO-2001/096372 A3 | 12/2001 |
| WO | WO-2003/075855 A2 | 9/2003 |
| WO | WO-2003/075855 A3 | 9/2003 |
| WO | WO-2004/010957 A2 | 2/2004 |
| WO | WO-2004/066933 A2 | 8/2004 |
| WO | WO-2004/067564 A2 | 8/2004 |
| WO | WO-2005/058961 A2 | 6/2005 |
| WO | WO-2007/120787 A2 | 10/2007 |
| WO | WO-2008/131376 A2 | 10/2008 |
| WO | 2012078688 A2 | 6/2012 |
| WO | WO-2012/078688 A2 | 6/2012 |
| WO | WO-2012/078688 A3 | 6/2012 |
| WO | 2012078688 A3 | 8/2012 |
| WO | 2012125712 A2 | 9/2012 |
| WO | 2012125712 A3 | 12/2012 |
| WO | 2013055874 A2 | 4/2013 |
| WO | 2013055874 A3 | 6/2013 |
| WO | 2013170263 A2 | 11/2013 |
| WO | 2014005704 A1 | 1/2014 |
| WO | 2013170263 A3 | 1/2015 |
| WO | 2015002134 A1 | 1/2015 |
| WO | 2015155976 A1 | 10/2015 |
| WO | WO-2009/068649 A2 | 12/2017 |
| WO | WO2019109007 A1 | 6/2019 |
| WO | 2020095249 A1 | 5/2020 |
| WO | 2020249483 A1 | 12/2020 |

OTHER PUBLICATIONS

Hurvitz et al. ("Hurvitz", J. of Clin. Oncology, 2013, 31, 1157-1163 and 2977) (Year: 2013).*
Swain et al. ("Swain", The Lancet Oncology, 2013, 14, 438-439) (Year: 2013).*
Raewyn Poole ("Poole", Drugs, 2014, 74, 1973-1981) (Year: 2014).*
Almagro, J.C. et al. (Jan. 1, 2008). "Humanization of Antibodies," *Frontiers in Bioscience* 13:1619-1633.
Amsberry, K.L. et al. (Nov. 1990). "The Lactonization of 2'-Hydroxyhydrocinnamic Acid Amides: A Potential Prodrug for Amines," *The Journal of Organic Chemistry* 55(23):5867-5877.
Arnold, R.S. et al. (2008). "Prostate Cancer Bone Metastasis: Reactive Oxygen Species, Growth Factors and Heparan Sulfate Proteoglycans Provide a Signaling Triad that Supports Progression," *AACR*, Annual Meeting, Abstract No. 4504, 1 page.
Balmaña, J. et al. (May 2009). "BRCA In Breast Cancer: ESMO Clinical Recommendations," *Annals of Oncology* 20 (supp 4):iv19-iv20.
Bhaskar, V. et al. (Oct. 1, 2003). "E-Selectin up-Regulation Allows For Targeted Drug Delivery In Prostate Cancer," *Cancer Research* 63:6387-6394.
Börresen-Dale, A-L. (2003). "Genetic Profiling Of Breast Cancer: From Molecular Portraits To Clinical Utility," *International Journal of Biological Markers* 18(1):54-56.
Brown, M. et al. (May 1, 1996). "Tolerance of Single, but not Multiple, Amino Acid Replacements in Antibody VH CDR 2: A Means of Minimizing B cell Wastage From Somatic Hypermutation?," *J. Immunol.*156(9):3285-3291.
Chari, R.V.J. et al. (Jan. 1, 1992). "Immunoconjugates Containing Novel Maytansinoids: Promising Anticancer Drugs," *Cancer Research* 52:127-131.
Chou, T.-C. (Jan. 15, 2010, e-pub. Jan. 12, 2010). "Drug Combination Studies and Their Synergy Quantification Using the Chou-Talaly Method," *Cancer Res* 70(2): 440-446.
Derisi, J. et al. (Dec. 1996). "Use of a cDNA microarray To Analyse Gene Expression Patterns In Human Cancer," *Nature Genetics* 14:457-460.
Doronina, S.O. et al. (Jul. 2003). "Development Of Potent Monoclonal Antibody Auristatin Conjugates For Cancer Therapy," *Nature Biotechnology* 21(7):778-784.
Dressman, M.A. et al. (2001). "Genes that Co-cluster with Estrogen Receptor Alpha in Microarray Analysis of Breast Biopsies," *The Pharmacogenomics Journal* 1(2):135-141.
Dubowchik, G.M. et al. (Aug. 1999). "Receptor-Mediated and Enzyme-Dependent Targeting of Cytotoxic Anticancer Drugs," *Pharm. Therapeutics* 83(2):67-123.
El-Tanani, M.K. et al. (Jul. 23, 1996)."Insulin/IGF-1 Modulation of the Expression of two Estrogen-induced Genes in MCF-7 Cells" *Molecular and Cellular Endocrinology* 121(1):29-35.
El-Tanani, M.K. et al. (Nov. 29, 1996). "Interaction Between Estradiol and cAMP in the Regulation of Specific Gene Expression," *Molecular and Cellular Endocrinology* 124(1-2):71-77.
El-Tanani, M.K. et al. (Mar. 1997). "Interaction Between Estradiol and Growth Factors in the Regulation of Specific Gene Expression in MCF-7 Human Breast Cancer Cells," *J. Steroid Biochem. Molec. Biol.* 60(5-6):269-276.
EMBL Database, (Dec. 23, 1995). Accession No. U41060.
Forero, A. et al. (Dec. 9-13, 2014). "SGN-LIV1A: A Phase 1 Trial Evaluating a Novel Antibody-Drug Conjugate in Patients with LIV-1-Positive Breast Cancer," Poster—Abstract No. 419 Presented at *San Antonio Breast Cancer Symposium*, San Antonio, TX, three pages.
Forero, A. et al. (Dec. 8-12, 2015). "Interim Analysis of a Phase 1 Study of the Antibody-Drug Conjugate SGN-LIV1A in Patients with Metastatic Breast Cancer," Poster-Abstract No. 638, Presented at Session: 621—New Drug and Treatment Strategies, San Antonio Breast Cancer Symposium; San Antonio, TX, three pages.
Forero, A. et al. (Dec. 6-10, 2016). "Phase 1 Study of the Antibody-Drug Conjugate (ADC) SGN-LIV1A in Patients with Heavily Pretreated Metastatic Breast Cancer," Poster-Abstract No. P6-12-

(56) References Cited

OTHER PUBLICATIONS

04, Presented at Session: 621—ew Drug and Treatment Strategies, San Antonio Breast Cancer Symposium; N, San Antonio, TX, three pages.
Francisco, J.A. et al. (2003, e-pub. May 8, 2003). "cAC10-vcMMAE, An Anti-CD30-Monomethyl Auristatin E Conjugate With Potent And Selective Antitumor Activity," *Blood* 102:1458-1465.
Hay, M.P. et al. (Aug. 2, 1999). "A 2-nitroimidazole Carbamate Prodrug of 5-amino-1-(chloromethyl)-3-[(5,6,7-trimethoxyindol-2-yl)carbonyl]-1,2-dihydro-3H-benz[e]indole (amino-seco-CBI-TMI) for Use With ADEPT and GDEPT," *Bioorganic & Medicinal Chemistry Letters* 9(15):2237-2242.
Johnson, D.A. et al. (Jul.-Aug. 1995). "Anti-Tumor Activity of CC49-Doxorubicin Immunoconjugates," *Anticancer Res.* 15(4):1387-1393.
Khan, J. et al. (1999). "Expression Profiling In Cancer Using cDNA Microarrays," *Electrophoresis* 20:223-229.
King, D.J. et al. (1992). "Expression, Purification and Characterization Of A Mouse-Human Chimeric Antibody and Chimeric Fab' Fragment," *Biochem. J.* 281:317-323.
Kingsbury, W.D. et al. (Nov. 1984). "A Novel Peptide Delivery System Involving Peptidase Activated Prodrugs as Antimicrobial Agents. Synthesis and Biological Activity of Peptidyl Derivatives of 5-Fluorouracil," *Journal of Medicinal Chemistry* 27(11):1447-1451.
Kobayashi, M. et al. (Mar. 1997). "Antitumor Activity Of TZT-1027, A Novel Dolastatin 10 Derivative," *Jpn. J. Cancer Res.* 88:316-327.
Kostelny, S.A. et al. (Mar. 1, 1992). "Formation of a Bispecific Antibody By The Use of Leucine Zippers," *J. Immunol.* 148(5):1547-1553.
Kostic, A. et al. (May 30-Jun. 3, 2014). "SGN-LIV1A, an Antibody-drug Conjugate, in Patients with LIV-1-positive Breast Cancer," Poster—Abstract No. TPS1143, *American Society of Clinical Oncology*, Chicago, IL, one page.
Lau, A. et al. (Oct. 1995). "Conjugation of Doxorubicin to Monoclonal Anti-Carcinoembryonic Antigen Antibody Via Novel Thiol-Directed Cross-Linking Reagents," *Bioorganic & Medicinal Chemistry* 3(10):1299-1304.
Lau, A. et al. (Oct. 1995). "Novel Doxorubicin-Monoclonal Anti-Carcinoembryonic Antigen Antibody Immunoconjugate Activity in vitro," *Bioorganic & Medicinal Chemistry* 3(10):1305-1312.
Li, F. et al. (Apr. 16-20, 2016). "Preclinical Combinations of the Antibody-drug Conjugate SGN-LIV1A with Chemotherapies Show Increased Activity," Poster—Abstract No. 2966 Presented at *AACR Annual Meeting*, New Orleans, LA, two pages.
Liefers, G.-J. et al. (Jul. 23, 1998). "Micrometastases and Survival In Stage II Colorectal Cancer," *New England J. Med.* 339(4):223-228.
Lue, H.-W. et al. (Apr. 12-16, 2008). "LIV-1 Mediates Epithelial to Mesenchymal Transition and Correlates with Prostatic Cancer Progression," *AAC, Annual Meeting*, Abstract No. 5373, 1 page.
Manning, D.L. et al. (1994). "Oestrogen-regulated Genes in Breast Cancer: Association of pLIV1 With Lymph Node Involvement," *European Journal of Cancer* 30A(5):675-678.
McClelland, R.A. et al. (1998). "Oestrogen-Regulated Genes in Breast Cancer: Association of pLIVI with Response to Endocrine Therapy," *Br. J. Cancer* 77(10):1653-1656.
Modi, S. et al. (Dec. 5-7, 2017). "Phase 1 Study of the Antibody-Drug Conjugate Ladiratuzumab Vedotin (SGN-LIV1A) in Patients with Heavily Pretreated Triple-Negative Metastatic Breast Cancer," Abstract No. PD3-14 Presented at Session 621, New Drugs and Treatment Strategies, San Antonio Breast Cancer Symposium, San Antonio, TX, three pages.
Mohammad, R.M. et al. (1999). "A New Tubulin Polymerization Inhibitor, Auristatin PE, Induces Tumor Regression In A Human Waldenstrom's Macroglobulinemia Xenograft Model," *Intl. J. Oncology* 15:367-372.

Neville, D.M. et al. (Sep. 5, 1989). "Enhancement of Immunotoxin Efficacy by Acid-cleavable Crosslinking Agents Utilizing Diphtheria Toxin and Toxin Mutants," *The Journal of Biological Chemistry* 264(25):14653-14661.
Payne, J.A. et al. (Jul. 28, 1995). "Primary Structure, Functional Expression, And Chromosomal Localization Of The Bumetanide-Sensitive Na—K—Cl Cotransporter In Human Colon," *J. Biol. Chem.* 270:17977-17985.
Pettit, G.R. et al. (1998). "Antineoplastic Agents 365. Dolastatin 10 SAR probes," *Anti-Cancer Design* 13:243-277.
Pollack, V.A. et al. (Aug. 2007, e-pub. Jun. 1, 2007). "Treatment Parameters Modulating Regression of Human Melanoma Xenografts by an Antibody—drug Conjugate (CR011-vcMMAE) Targeting GPNMB," *Cancer Chemother. Pharmacol.* 60(3):423-435.
Reichert, J.M. et al. (May 2007). "Development Trends for Monoclonal Antibody Cancer Therapeutics," *Nat. Rev. Drug Disc.* 6(5):349-356.
Rodrigues, M.L. et al. (Apr. 1995). "Synthesis and β-lactamase-mediated Activation of a Cephalosporin-Taxol Prodrug," *Chemistry & Biology* 2(4):223-227.
Ross, S. et al. (May 1, 2002). "Prostate Stem Cell Antigen As Therapy Target: Tissue Expression and In Vivo Efficacy Of An Immunoconjugate," *Cancer Research* 61:2546-2553.
Rudikoff, S. et al. (Mar. 1, 1982). "Single Amino Acid Substitution Altering Antigen-binding Specificity," *Proc. Nat'l Acad. Sci. USA* 79(6):1979-1983.
Smith, L.M. et al., "LIV-1 Antibody-Drug Conjugate: A Novel Therapeutic Agent for Breast Cancer," *CTRC-AACR San Antonio Breast Cancer Symposium*, Abstract No. 851651, 1 page, (2010).
Songsivilai, S. et al. (1990). "Bispecific Antibody: A Tool for Diagnosis and Treatment of Disease," *Clin. Exp. Immunol.* 79:315-321.
Storm, D.R. et al. (Aug. 1972). "Effect of Small Changes in Orientation on Reaction Rate," *Journal of the American Chemical Society* 94(16):5815-5825.
Sussman, D. et al. (Apr. 2-6, 2011). "LIV-1 Antibody-Drug Conjugate: A Novel Therapeutic Agent for Breast and Prostate Cancer," Poster—Abstract No. 3620 Presented at AACR, one page.
Sussman, D. et al. (Apr. 6-10, 2013)."SGN-LIV1A: A Development Stage Antibody-Drug Conjugate Targeting LIV-1 for the Treatment of Metastatic Breast Cancer," Presented at AACR, Annual Meeting, Cancer Res 73(8 Suppl):Abstract No. 3962, 1 page.
Sussman, D. et al. (2014; e-published on Sep. 24, 2014). "SGN-LIV1A: A Novel Antibody—Drug Conjugate Targeting LIV-1 for the Treatment of Metastatic Breast Cancer," *Molecular Cancer Therapeutics* 13(12):2991-3000.
Taylor, K.M. et al. (1999). "The LIV-1 Gene, Implicated In Metastatic Breast Cancer, Codes For A Histidine-Rich Transmembrane Protein," *British Journal of Cancer* 80(Suppl 2):24.
Taylor, K.M. (Apr. 2000). "Hypothesis Paper: LIV-1 Breast Cancer Protein Belongs to New Family of Histidine-Rich Membrane Proteins with Potential to Control Intracellular Zn2+ Homeostasis," *IUBMB Life* 49(4):249-253.
Taylor, K.M. et al. (Apr. 1, 2003). "The LZT Proteins; the LIV-1 Subfamily of Zinc Transporters," *Biochimica et Biophysica Acta* 1611(1-2):16-30.
Taylor, K.M. et al. (Nov. 2003). "Structure-function Analysis of LIV-1, the Breast Cancer-associated Protein that Belongs to a New Subfamily of Zinc Transporters," *Biochem. J.* 375(1):51-59.
Thorpe, P.E. et al. (Nov. 15, 1987). "New Coupling Agents for the Synthesis of Immunotoxins Containing a Hindered Disulfide Bond with Improved Stability in Vivo" *Cancer Research* 47:5924-5931.
Tse, K.F. et al. (Feb. 15, 2006). "CR011, a Fully Human Monoclonal Antibody-Auristatin E Conjugate, for the Treatment of Melanoma," *Clin. Cancer Res* 12(4):1373-1382.
Unno, J. et al. (Oct. 2009). "LIV-1 Enhances the Aggressive Phenotype Through the Induction of Epithelial to Mesenchymal Transition in Human Pancreatic Carcinoma Cells," *International Journal of Oncology* 35(4):813-821.
Welford, S.M. et al. (1998). "Detection Of Differentially Expressed Genes In Primary Tumor Tissues Using Representational Differences Analysis Coupled To Microarray Hybridization," *Nucleic Acids Research* 26(12):3059-3065.

(56) References Cited

OTHER PUBLICATIONS

Williams, K. et al. (1998). "Analysis Of Differential Expression In Normal and neoplastic Human Breast Epithelial Cell Lines," *Electrophoresis* 19:333-343.

Yamamoto, K. et al. (Mar. 1996). "Clinical Application Of Chimeric Monoclonal Antibody A7-NCS Conjugate," *Biotherapy* 10:365-367, Abstract.

Yang, G.P. et al. (1999). "Combining SSH and cDNA microarrays For Rapid Identification Of Differentially Expressed Genes," *Nucleic Acids Research* 27(6):1517-1523.

EPO Application No. 11847198.6, European Search Report and Supplementary European Search Opinion dated Apr. 16, 2015.

EPO Application No. EP16200557.3, European Search Report and Written Opinion of the International Searching Authority dated Jan. 25, 2017.

EPO Application No. 18204152.5, European Extended Search Report dated Dec. 4, 2018.

U.S. Appl. No. 13/990,778, Non-Final Office Action dated Apr. 14, 2015.

U.S. Appl. No. 13/990,778, Notice of Allowance dated Sep. 18, 2015.

U.S. Appl. No. 14/052,905, Non-Final Office Action dated Feb. 25, 2014.

U.S. Appl. No. 14/052,905, Notice of Allowance dated Aug. 8, 2014.

U.S. Appl. No. 14/052,905, Requirement for Restriction/Election dated Nov. 12, 2013.

U.S. Appl. No. 14/052,905, Response to Non-Final Office Action filed Jun. 19, 2014.

U.S. Appl. No. 14/052,905, Response to Requirement for Restriction/Election filed Dec. 12, 2013.

U.S. Appl. No. 14/948,183, Non-Final Office Action dated Feb. 2, 2017.

U.S. Appl. No. 14/948,183, Notice of Allowance dated May 31, 2017.

WIPO Application No. PCT/US2011/063612, PCT International Preliminary Reporton Patentability dated Jun. 20, 2013.

WIPO Application No. PCT/US2011/063612, PCT International Search Report and Written Opinion of the International Searching Authority dated Jun. 27, 2012.

WIPO Application No. PCT/US2017/22541, PCT International Search Report and Written Opinion of the International Searching Authority dated Jul. 31, 2012.

Anonymous (Feb. 25, 2016). "A Safety Study of SGN-LIV1A in Breast Cancer Patients Histroy of Changes for the Study: NCT01969643," retrived from URL:https://clinicaltrials.gov/ct2/history/NTC019696437A=328C=Side-by-Side#StudyPageTop, last visited Oct. 17, 2019, 7 pages.

Bedognetti, D. et al. (2016, e-pub. Apr. 26, 2016). "Checkpoint Inhibitors and Their Application in Breast Cancer," Breast Care 11(2):108-115.

Cao, A. et al.(Apr. 20, 2016). "Abstract 4914: Auristatin-Based Antibody Drug Conjugates Activate Multiple ER Stress Response Pathways Resulting in Immunogenic Cell Death and Amplified T-Cell Responses," Retrieved from the Internet: URL:https://cancerres.aacrjournals.org/content/76/14_Supplement/4914, last visited Mar. 6, 2020, 4 pages.

Extended Search Report, dated Apr. 6, 2020, for European Patent Application No. 17767448.8, 17 pages.

Müller, P. et al. (Aug. 1, 2014). "Cancer Chemotherapy Agents Target Intratumoral Dendritic Ceils to Potentiate Antitumor Immunity," OncoImmunology 3(8):e954460, 3 pages.

Nanda, R. et al. (Jul. 20, 2016, e-pub. May 2, 2016). "Pembrolizumab in Patients Wth Advanced Triple-Negative Breast Cancer: Phase Ib KEYNOTE-012 Study", J. Clin. Oncology 34(21):2460-2467.

Partial Supplementary European Search Report, dated Nov. 27, 2019, for European Patent. Application No. 17767448.8, 16 pages.

Vogel, C.-W. (1987). Immunoconjugates: Antibody Conjugates in Radioimaging and herapy Of Cancer, Oxford University Press, New York, Oxford pp. 1-380.

Wang, H. et al., (Mar. 1, 2004). "Pretreatment With Dexamethasone Increase Antitumor Activity of Carboplatin and Gemcitabine in Mice Bearing Human Cancer Xenografts: In Vivo Activity, Pharmacokinetics, and Clinical Implications for Cancer Chemotherapy," Clinical Cancer Research 10(5):1633-1644.

Wawrzynczak et al. (1987). "Methods for Preparing Immunotoxins: Effect of the Linkage on Activity and Stability," in Immunoconjugates: Antibody Conjugates in Radioimagery and Therapy of Cancer, pp. 28-55.

(2003). "Doxycycline," in RLE Drug Encyclopedia ed.10, pp. 299-300, 9 pages.

Criscitiello, C. et al. (2015). "Immunotherapy of Breast Cancer," Immuno-Oncology Prog. Tumor Res. 42:30-43.

\* cited by examiner

COMBINATION THERAPY USING A LIV1-ADC AND A CHEMOTHERAPEUTIC

CROSS REFERENCE TO RELATED APPLICATIONS

This application is a national stage application under 35 U.S.C. § 371 of International Application No. PCT/US2017/022541, with the International Filing Date of Mar. 15, 2017, which claims priority to U.S. Provisional Application No. 62/308,639, filed on Mar. 15, 2016, U.S. Provisional Application No. 62/317,792, filed on Apr. 4, 2016, and U.S. Provisional Application No. 62/367,510 filed Jul. 27, 2016, the disclosures of which are incorporated herein by reference in their entirety.

REFERENCE TO A SEQUENCE LISTING

A sequence listing designated 0710-00313PC Sequence Listing ST25.txt of 16 KB created Mar. 1, 2017, is incorporated herein by reference.

FIELD OF THE INVENTION

This invention relates to methods for the treatment of cancer comprising administering a LIV1-ADC and a chemotherapeutic.

BACKGROUND

LIV-1 is a member of the LZT (LIV-1-ZIP Zinc Transporters) subfamily of zinc transporter proteins. Taylor et al., Biochim. Biophys. Acta 1611:16-30 (2003). Computer analysis of the LIV-1 protein reveals a potential metalloprotease motif, fitting the consensus sequence for the catalytic zinc-binding site motif of the zinc metalloprotease. LIV-1 mRNA is primarily expressed in breast, prostate, pituitary gland and brain tissue.

The LIV-1 protein has also been implicated in certain cancerous conditions, e.g. breast cancer and prostate cancer. The detection of LIV-1 is associated with estrogen receptor-positive breast cancer, McClelland et al., Br. J. Cancer 77:1653-1656 (1998), and the metastatic spread of these cancers to the regional lymph nodes. Manning et al., Eur. J. Cancer 30A:675-678 (1994).

SGN-LIV1A is a LIV-1-directed antibody-drug conjugate (ADC) consisting of three components: 1) the humanized antibody hLIV22, specific for human LIV-1, 2) the microtubule disrupting agent monomethyl auristatin E (MMAE), and 3) a stable linker, valine-citrulline (vc), that covalently attaches MMAE to hLIV22. The proposed mechanism of action (MOA) is initiated by SGN-LIV1A binding to LIV-1 on the cell surface followed by internalization of the ADC. Upon trafficking to lysosomes, the delivered drug (MMAE) is released through proteolytic degradation of the vc linker. Binding of the released drug to tubulin disrupts the microtubule network, leading to cell cycle arrest and apoptosis.

SGN-LIV1A has been shown to reduce tumor volumes in vivo, and is currently being evaluated in a phase 1 clinical trial for patients with LIV-1-positive metastatic breast cancer. However, improvements are needed in cancer therapy. The present invention solves this and other problems.

SUMMARY OF THE CLAIMED INVENTION

The invention provides a method for treating a subject having or at risk of cancer. The method includes administering to the subject a LIV-1 antibody drug conjugate (LIV-1-ADC) and a chemotherapeutic. The LIV-1-ADC includes a humanized hLIV22 antibody conjugated to a vcMMAE (valine-citrulline-monomethyl auristatin E), and the chemotherapeutic is one of carboplatin, doxorubicin, paclitaxel, trastuzumab, and an mTOR inhibitor. Optionally, the subject has prostate cancer, ovarian cancer, endometrial cancer, pancreatic cancer, lung cancer, a cervical cancer, a melanoma, squamous cell carcinoma, or a breast cancer, such as triple negative breast cancer, triple positive breast cancer, HER2-positive breast cancer, or hormone receptor positive breast cancer.

In some embodiments, the LIV-1-ADC is administered at a dosage between 1.5 mg/kg and 4 mg/kg of the subject's body weight. In an embodiment, the LIV-1-ADC is administered at a dosage of 2.5 mg/kg of the subject's body weight. In an embodiment, the LIV-1-ADC is administered once every 3 weeks. In an embodiment, the LIV-1-ADC is administered by intravenous injection.

In an embodiment, the chemotherapeutic is carboplatin, and is administered at a dosage between 200 mg/m$^2$ and 750 mg/m$^2$. In an embodiment, the carboplatin is administered by intravenous injection. In another embodiment, the chemotherapeutic is doxorubicin, and is administered at a dosage between 40 mg/m$^2$ and 80 mg/m$^2$. In an embodiment, the doxorubicin is administered by intravenous injection. In another embodiment, the chemotherapeutic is paclitaxel, and is administered at a dosage between 100 mg/m$^2$ to 260 mg/m$^2$. In an embodiment, the paclitaxel is administered by intravenous injection.

The invention also provides methods for treating a subject having or at risk of cancer, the method comprising administering to the subject a LIV-1 antibody drug conjugate (LIV-1-ADC) and either trastuzumab emtansine or pertuzumab. The LIV-1-ADC includes a humanized hLIV22 antibody conjugated to a vcMMAE (valine-citrulline-monomethyl auristatin E).

DEFINITIONS

Figure 1:
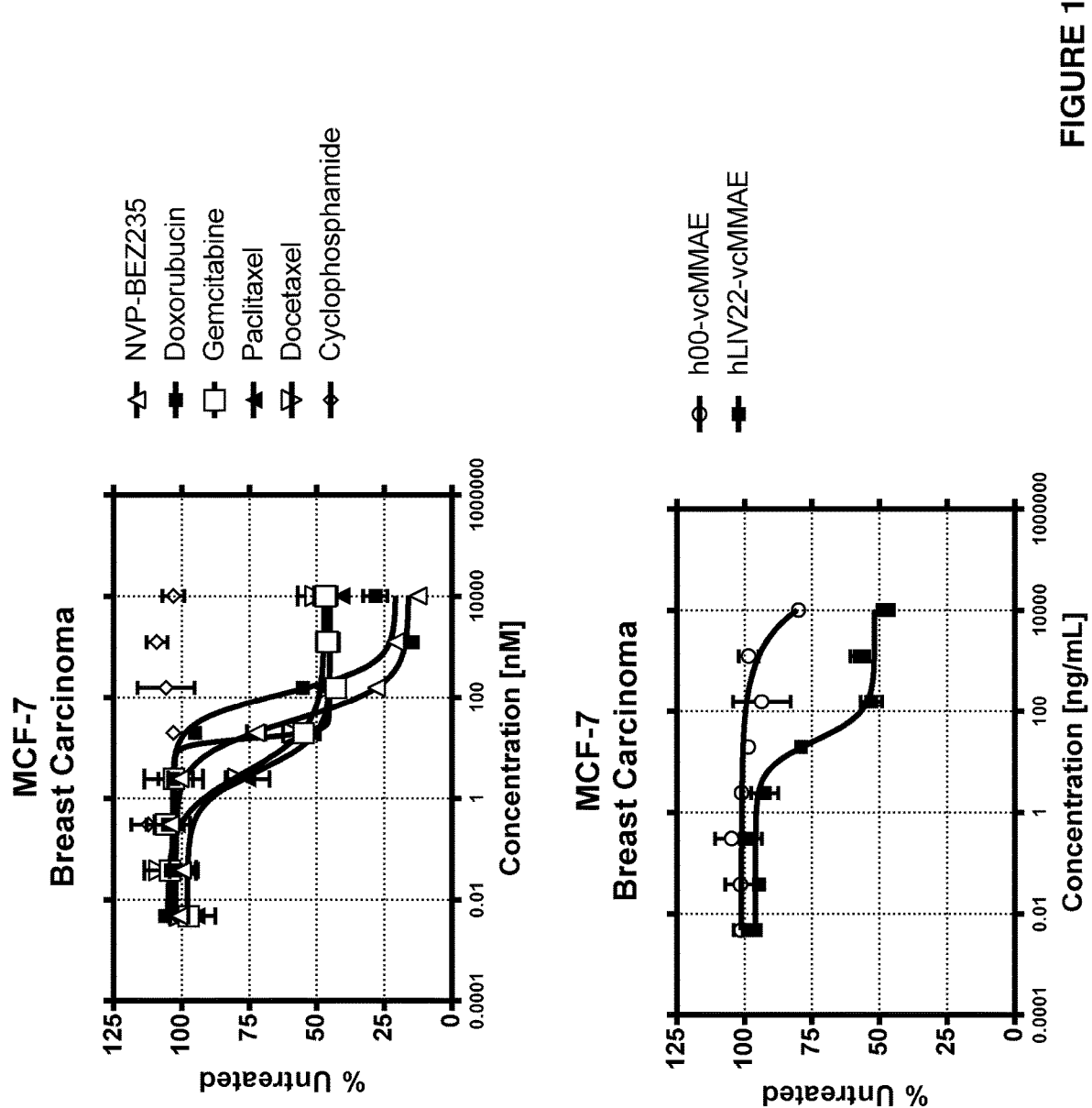
FIG. 1 shows the viability of multiple agents on MCF-7 cells, according to an embodiment of the invention.

The term "antibody" includes intact antibodies and binding fragments thereof. Typically, antibody fragments compete with the intact antibody from which they were derived for specific binding to the target including separate heavy chains, light chains Fab, Fab', F(ab')$_2$, F(ab)c, diabodies, Dabs, nanobodies, and Fv. Fragments can be produced by recombinant DNA techniques, or by enzymatic or chemical separation of intact immunoglobulins. The term "antibody" also includes a diabody (homodimeric Fv fragment) or a minibody ($V_L$-$V_H$-$C_H3$), a bispecific antibody or the like. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)). The term "antibody" includes an antibody by itself (naked antibody) or an antibody conjugated to a cytotoxic or cytostatic drug.

A "cytotoxic effect" refers to the depletion, elimination and/or the killing of a target cell. A "cytotoxic agent" refers to an agent that has a cytotoxic effect on a cell. Cytotoxic agents can be conjugated to an antibody or administered in combination with an antibody.

A "cytostatic effect" refers to the inhibition of cell proliferation. A "cytostatic agent" refers to an agent that has a cytostatic effect on a cell, thereby inhibiting the growth and/or expansion of a specific subset of cells. Cytostatic agents can be conjugated to an antibody or administered in combination with an antibody.

The term "pharmaceutically acceptable" as used herein refers to those compounds, materials, compositions, and/or dosage forms that are, within the scope of sound medical judgment, suitable for contact with the tissues of human beings and animals without excessive toxicity, irritation, allergic response, or other problems or complications commensurate with a reasonable benefit/risk ratio. The term "pharmaceutically compatible ingredient" refers to a pharmaceutically acceptable diluent, adjuvant, excipient, or vehicle with which an anti-LIV-1 antibody is administered.

The phrase "pharmaceutically acceptable salt," refers to pharmaceutically acceptable organic or inorganic salts of an anti-LIV-1 antibody or conjugate thereof or agent administered with an anti-LIV-1 antibody. Exemplary salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Multiple counter ions may occur in instances where multiple charged atoms are part of the pharmaceutically acceptable salt. Hence, a pharmaceutically acceptable salt can have one or more charged atoms and/or one or more counterion.

The term "effective amount" refers to the amount of a LIV-1-ADC, e.g., SGN-LIV1A, that is sufficient to inhibit the occurrence or ameliorate one or more clinical or diagnostic symptoms of a LIV-1-associated disorder in a subject. An effective amount of an agent is administered according to the methods described herein in an "effective regimen." The term "effective regimen" refers to a combination of amount of the agent and dosage frequency adequate to maintain high LIV-1 occupancy, which may accomplish treatment or prevention of a LIV-1-associated disorder. In a preferred embodiment, an effective regimen maintains near complete, e.g., greater than 90%, LIV-1 occupancy on LIV-1-expressing cells during dosing intervals.

The terms "treatment" and "therapy," and the like, as used herein, are meant to include therapeutic or suppressive measures for a disease or disorder leading to any clinically desirable or beneficial effect, including, but not limited to, alleviation or relief of one or more symptoms, regression, slowing or cessation of progression of the disease or disorder. For example, treatment can include a decrease or elimination of a clinical or diagnostic symptom of a LIV-1-expressing disorder after the onset of the clinical or diagnostic symptom by administration of an anti-LIV-1 antibody or other LIV-1 binding agent to a subject. Treatment can be evidenced as a decrease in the severity of a symptom, the number of symptoms, or frequency of relapse.

Except when noted, the terms "subject" or "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the LIV-1 binding agents of the invention can be administered. In preferred embodiments, the terms subject or patient are used to refer to human patients. Subjects of the present invention include those that have been diagnosed with a LIV-1 expressing cancer, including, for example, breast cancer, prostate cancer, ovarian cancer, endometrial cancer, pancreatic cancer, lung cancer, cervical cancer, a melanoma, or squamous cell carcinoma. In certain embodiments, the subject will have a refractory or relapsed LIV-1 expressing cancer.

Compositions or methods "comprising" one or more recited elements may include other elements not specifically recited. For example, a composition that comprises antibody may contain the antibody alone or in combination with other ingredients.

Designation of a range of values includes all integers within or defining the range.

As used herein, the term "about" denotes an approximate range of plus or minus 10% from a specified value. For instance, the language "about 20%" encompasses a range of 18-22%. As used herein, about also includes the exact amount. Hence, "about 20%" means "about 20%" and also "20%.

DETAILED DESCRIPTION

I. General

The invention provides methods for treating cancer, in particular breast cancer.

The present inventors have discovered that combination therapy with two different classes of anticancer compounds: antibody-drug conjugate compounds and chemotherapeutic agents, can improve a therapeutic benefit for subjects suffering from cancer. In particular, the present inventors have found that combination therapy with (1) an anti-LIV-1 antibody conjugated to an auristatin compound and (2) a chemotherapeutic agent provides synergistic therapeutic effects in the treatment of cancer.

II. LIV-1-ADC

Unless otherwise indicated, a LIV-1-antibody drug conjugate (LIV-1-ADC) includes an antibody specific for the human LIV-1 protein conjugated to a cytotoxic agent. An exemplary human LIV-1 sequence is assigned Swiss Prot accession number Q13433. Q13433 is included herein as SEQ ID NO:1. Three variant isoforms and one polymorphism are known. A second version of the human LIV-1 protein, accession number AAA96258.2, is included herein as SEQ ID NO:2. Four extracellular domains are bounded by residues 29-325, 377-423, 679-686 and 746-755 of Q13433 respectively.

SGN-LIV1A is a LIV-1-directed antibody-drug conjugate (ADC) produced by the conjugation of the drug linker vcMMAE (monomethyl auristatin E with a valine-citrulline linker) to the humanized antibody hLIV22. hLIV22 is a humanized form of the mouse BR2-22a antibody, described in U.S. Pat. No. 9,228,026. The hLIV22 antibody is essentially the same as BR2-22a within experimental error and contains seven back mutations. Methods of making the hLIV22 antibody are also disclosed in U.S. Pat. No. 9,228,026. The amino acid sequence of the light chain variable region of hLIV22 is provided herein as SEQ ID NO: 3. The amino acid sequence of the heavy chain variable region of hLIV22 is provided herein as SEQ ID NO: 4. Synthesis and conjugation of the drug linker vcMMAE (shown below; also referred to as 1006) are further described in U.S. Pat. No. 9,228,026 and US Patent Pub. No. 20050238649.

cell growth, while at the same time are tolerated by the subject. In an embodiment, administration of the combination decreases the toxic effects caused by administration of a chemotherapeutic agent alone. In some embodiments, the combination of SGN-LIV1A and a chemotherapeutic agent is synergistic or additive. For some combinations, each agent in the combination can be effectively administered at lower levels than when administered alone.

As discussed above, the combination therapies of the invention can be used to treat cancer. Some such cancers show detectable levels of LIV-1 measured at either the protein (e.g., by immunoassay using one of the exemplified antibodies) or mRNA level. Some such cancers show elevated levels of LIV-1 relative to noncancerous tissue of the same type, preferably from the same patient. An exemplary level of LIV-1 on cancer cells amenable to treatment is 5000-150000 LIV-1 molecules per cell, although higher or lower levels can be treated. Optionally, a level of LIV-1 in a cancer is measured before performing treatment.

Examples of cancers associated with LIV-1 expression and amenable to treatment with the combination therapies of the invention include breast cancer, prostate cancer, ovarian cancer, endometrial cancer, pancreatic cancer, cervical, liver, gastric, kidney, and squamous cell carcinomas (e.g., bladder, head, neck and lung), skin cancers, e.g., melanoma, small

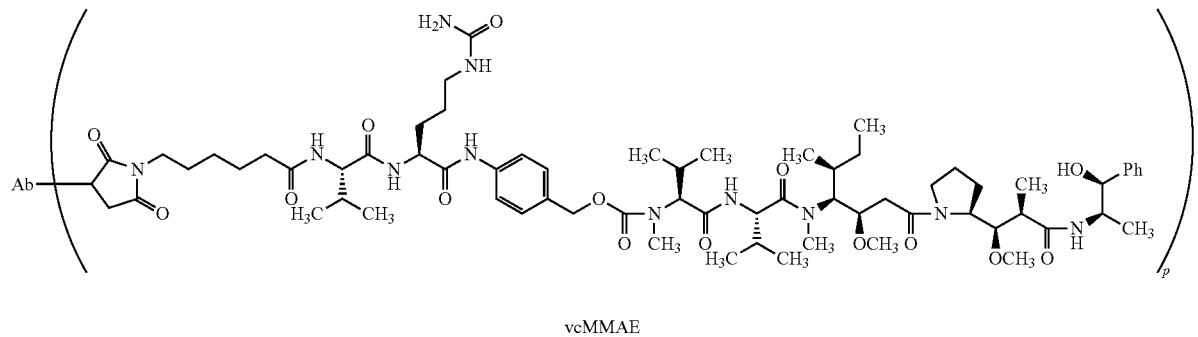

vcMMAE

III. Combination Therapy of Chemotherapeutic Agents and LIV-1-ADC

Cancer can be treated using a combination of SGN-LIV1A and a chemotherapeutic agent. The chemotherapeutic agent is either carboplatin, doxorubicin or paclitaxel, trastuzumab, a checkpoint inhibitor, or an mTOR inhibitor (such as Everolimus). Carboplatin (PARAPLATIN®; Bristol Myers Squibb, New York, N.Y.) is an alkylating agent. Doxorubicin (ADRIAMYCIN®, RUBEX®, DOXIL®, MYOCEL®, or CAELYX®) is an anthracycline antibiotic with antineoplastic activity. Paclitaxel (ABRAXANE®; Celgene, Summit, N.J.) is a taxane that inhibits microtubule breakdown. Trastuzumab (HERCEPTIN®; Genentech, South San Francisco, Calif.) is a monoclonal antibody that binds the HER2 receptor. Examples of checkpoint inhibitors (inhibitors that block immune checkpoints) include antibodies such as anti-PD-1 antibodies (e.g., MEDI0680, AMP-224, nivolumab, pembrolizumab, and pidilizumab), anti-PD-L1 antibodies (e.g., MEDI4736 and MPDL3280A), and anti-CTLA4 antibodies (e.g., ipilimumab and tremelimumab). Other checkpoint inhibitors/activators include B7-DC-Fc, LAG3 and TIM3.

The combination of SGN-LIV1A and a chemotherapeutic agent can be given to subjects at levels that inhibit cancer lung cell carcinoma or lung carcinoid. The treatment can be applied to patients having primary or metastatic tumors of these kinds. The treatment can also be applied to patients who are refractory to conventional treatments (e.g., for breast cancer: hormones, tamoxifen, HERCEPTIN®), or who have relapsed following a response to such treatments. The methods can also be used on triple negative breast cancers. A triple negative breast cancer is a term of art for a cancer lacking detectable estrogen and progesterone receptors and lacking overexpression of HER2/neu when stained with an antibody to any of these receptors, such as described in the examples. The methods can also be used on triple positive breast cancers, hormone receptor positive breast cancers, and HER2 positive breast cancers. Staining can be performed relative to an irrelevant control antibody and lack of expression shown from a background level of straining the same or similar to that of the control within experimental error. Likewise, lack of overexpression is shown by staining at the same or similar level within experimental error of noncancerous breast tissue, preferably obtained from the same patient. Alternatively or additionally, triple negative breast cancers are characterized by lack of responsiveness to hormones interacting with these receptors, aggressive behavior and a distinct pattern of metastasis.

In some embodiments, SGN-LIV1A and a chemotherapeutic agent are administered in such a way that the combination provides a synergistic or additive effect in the treatment of LIV-1-associated cancer in a patient. Administration can be by any suitable means provided that the administration provides the desired therapeutic effect. In preferred embodiments, SGN-LIV1A and a chemotherapeutic agent are administered during the same cycle of therapy, e.g., during one cycle of therapy, e.g., a three or four week time period.

SGN-LIV1A and a chemotherapeutic agent are administered in an effective regime meaning a dosage, route of administration and frequency of administration that delays the onset, reduces the severity, inhibits further deterioration, and/or ameliorates at least one sign or symptom of cancer. If a patient is already suffering from cancer, the regime can be referred to as a therapeutically effective regime. If the patient is at elevated risk of the cancer relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for SGN-LIV1A are 0.1 mg/kg to 50 mg/kg of the patient's body weight, more typically 1 mg/kg to 30 mg/kg, 1 mg/kg to 20 mg/kg, 1 mg/kg to 15 mg/kg, 1 mg/kg to 12 mg/kg, 1 mg/kg to 10 mg/kg, 2 mg/kg to 30 mg/kg, 2 mg/kg to 20 mg/kg, 2 mg/kg to 15 mg/kg, 2 mg/kg to 12 mg/kg, 2 mg/kg to 10 mg/kg, 3 mg/kg to 30 mg/kg, 3 mg/kg to 20 mg/kg, 3 mg/kg to 15 mg/kg, 3 mg/kg to 12 mg/kg, or 3 mg/kg to 10 mg/kg. In some methods, the patient is administered a dose of at least 1.5 mg/kg, at least 2 mg/kg or at least 3 mg/kg, administered once every three weeks or greater. In an embodiment, the patient is administered a dose of 2.5 mg/kg. In a further embodiment, the patient is administered a dose of 2.5 mg/kg, administered once every three weeks. The dosage depends on the frequency of administration, condition of the patient and response to prior treatment, if any, whether the treatment is prophylactic or therapeutic and whether the disorder is acute or chronic, among other factors.

In combination with carboplatin, SGN-LIV1A is administered at a dose between 0.5 mg/kg and 6 mg/kg. Other appropriate dose ranges of SGN-LIV1A in the combination are 1 mg/kg to 5 mg/kg, and 2 mg/kg to 3 mg/kg. In an embodiment, SGN-LIV1A is administered at a dose of 2.5 mg/kg in combination with carboplatin. In combination with SGN-LIV1A, carboplatin is administered at a dose between 100 mg/m$^2$ and 950 mg/m$^2$. Other appropriate dose ranges of carboplatin in the combination are 200 mg/m$^2$ to 750 mg/m$^2$, and 300 mg/m$^2$ to 600 mg/m$^2$. In an embodiment, carboplatin is administered at a dose of 300 mg/m$^2$ in combination with SGN-LIV1A. In another embodiment, carboplatin is administered at a dose of AUC 6 IV in combination with SGN-LIV1A.

In combination with doxorubicin, SGN-LIV1A is administered at a dose between 0.5 mg/kg and 6 mg/kg. Other appropriate dose ranges of SGN-LIV1A in the combination are 1 mg/kg to 5 mg/kg, and 2 mg/kg to 3 mg/kg. In an embodiment, SGN-LIV1A is administered at a dose of 2.5 mg/kg in combination with doxorubicin. In combination with SGN-LIV1A, doxorubicin is administered at a dose between 30 mg/m$^2$ and 90 mg/m$^2$. Other appropriate dose ranges of doxorubicin in the combination are 40 mg/m$^2$ to 80 mg/m$^2$, and 60 mg/m$^2$ to 75 mg/m$^2$. In an embodiment, doxorubicin is administered at a dose of 60 mg/m$^2$ in combination with SGN-LIV1A.

In combination with paclitaxel, SGN-LIV1A is administered at a dose between 0.5 mg/kg and 6 mg/kg. Other appropriate dose ranges of SGN-LIV1A in the combination are 1 mg/kg to 5 mg/kg, and 2 mg/kg to 3 mg/kg. In an embodiment, SGN-LIV1A is administered at a dose of 2.5 mg/kg in combination with paclitaxel. In combination with SGN-LIV1A, paclitaxel is administered at a dose between 50 mg/m$^2$ and 300 mg/m$^2$. Other appropriate dose ranges of paclitaxel in the combination are 100 mg/m$^2$ to 260 mg/m$^2$, and 135 mg/m$^2$ to 175 mg/m$^2$. In an embodiment, paclitaxel is administered at a dose of 175 mg/m$^2$ in combination with SGN-LIV1A. In another embodiment, paclitaxel is administered at a dose of 80 mg/m$^2$ in combination with SGN-LIV1A.

In combination with trastuzumab, SGN-LIV1A is administered at a dose between 0.5 mg/kg and 2.8 mg/kg. In an embodiment, SGN-LIV1A is administered at a dose between 1 mg/kg and 2.8 mg/kg in combination with trastuzumab. In another embodiment, SGN-LIV1A is administered at a dose of 2.5 mg/kg in combination with trastuzumab. In an embodiment, SGN-LIV1A is administered once a week. In another embodiment, SGN-LIV1A is administered once every three weeks. In an embodiment, in combination with SGN-LIV1A, trastuzumab is administered at an initial dose of 8 mg/kg over a 90 minute IV infusion, and then 6 mg/kg over 30-90 minutes of an IV infusion. In a further embodiment, the 6 mg/kg over 30-90 minutes of an IV infusion is administered every 3 weeks. In a further embodiment, the 6 mg/kg over 30-90 minutes of an IV infusion is administered every 3 weeks for 52 weeks. In another embodiment, in combination with SGN-LIV1A, trastuzumab is administered at an initial dose 4 mg/kg over a 90 minute IV infusion, and then 2 mg/kg over a 30 minute IV infusion. In a further embodiment, the 2 mg/kg over a 30 minute IV infusion is administered once a week. In a further embodiment, the 2 mg/kg over a 30 minute IV infusion is administered once a week for 52 weeks.

In combination with a checkpoint inhibitor, SGN-LIV1A is administered at a dose between 0.5 mg/kg and 2.8 mg/kg. In an embodiment, SGN-LIV1A is administered at a dose between 1 mg/kg and 2.8 mg/kg in combination with trastuzumab. In another embodiment, SGN-LIV1A is administered at a dose of 2.5 mg/kg in combination with trastuzumab. In an embodiment, SGN-LIV1A is administered once a week. In another embodiment, SGN-LIV1A is administered once every three weeks.

Administration of SGN-LIV1A, carboplatin, doxorubicin, paclitaxel, trastuzumab, or an mTOR inhibitor can be parenteral, intravenous, oral, subcutaneous, intra-arterial, intracranial, intrathecal, intraperitoneal, topical, intranasal or intramuscular. In an embodiment, SGN-LIV1A is administered by intraperitoneal injection. In another embodiment, SGN-LIV1A is administered by intravenous injection. In another embodiment, carboplatin is administered by intravenous injection. In another embodiment, paclitaxel is administered by intravenous injection. In another embodiment, doxorubicin is administered by intravenous injection. Administration can also be localized directly into a tumor. Administration into the systemic circulation by intravenous or subcutaneous administration is preferred. Intravenous administration can be, for example, by infusion over a period such as 30-90 min or by a single bolus injection.

The frequency of administration of each agent of the combination (SGN-LIV1A, carboplatin, doxorubicin, paclitaxel, trastuzumab, or an mTOR inhibitor) depends on its half-life in the circulation, the condition of the patient and the route of administration among other factors. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are between weekly or three out of every four weeks over a continuous course of treatment, although more or less frequent dosing is also possible. In an embodiment, one or both agents of the combination is administered once every three weeks. In another embodiment, one or both agents of the combination is administered once every four weeks. For subcutaneous administration, an exemplary dosing frequency is daily to monthly, although more or less frequent dosing is also possible.

The number of dosages of SGN-LIV1A administered depends on the nature of the cancer (e.g., whether presenting acute or chronic symptoms) and the response of the disorder to the treatment. For acute disorders or acute exacerbations of a chronic disorder between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration of SGN-LIV1A are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, SGN-LIV1A can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively SGN-LIV1A can be in lyophilized form for constitution with a suitable vehicle, e.g., sterile pyrogen-free water, before use. The concentration of SGN-LIV1A in a liquid formulation can be e.g., 1-100 mg/ml, such as 10 mg/ml.

Treatment with the combination therapies of the invention can be further combined with additional chemotherapy, radiation, stem cell treatment, surgery other treatments effective against the disorder being treated. Useful classes of other agents that can be administered with the combination therapies of the invention include, for example, antibodies to other receptors expressed on cancerous cells, including other antibodies to the HER2 receptor (e.g., rastuzumab emtansine (KADCYLA®, Genentech, South San Francisco, Calif.), antitubulin agents (e.g., auristatins), pertuzumab (PERJETA®, Genentech, South San Francisco, Calif.)), or other antibody drug conjugates such as sacituzumab govitecan, checkpoint inhibitors (e.g., anti-PD-1, anti-PD-L1), DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Treatment with the combination therapies of the invention can increase the median progression-free survival or overall survival time of patients with tumors (e.g., breast, prostate, melanoma), especially when relapsed or refractory, by at least 30% or 40% but preferably 50%, 60% to 70% or even 100% or longer, compared to the same treatment (e.g., chemotherapy) but without the combination therapies of the invention. In addition or alternatively, treatment (e.g., standard chemotherapy) including the combination therapies of the invention can increase the complete response rate, partial response rate, or objective response rate (complete+partial) of patients with tumors by at least 30% or 40% but preferably 50%, 60% to 70% or even 100% compared to the same treatment (e.g., chemotherapy) but without the combination therapies of the invention.

All patent filings, website, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

The following examples are offered to illustrate, but not to limit the claimed invention.

I. In Vitro Cytotoxicity Assay and Combination Assays

Materials

Docetaxel, paclitaxel, doxorubicin, gemcitabine, and NVP-BEZ235 were purchased from LC Laboratories (Woburn, Mass.) and reconstituted in DMSO for in vitro assays. Cyclophosphamide was purchased from Selleckchem (Houston, Tex.). SGN-LIV1A was conjugated with average of 4 MMAE per antibody. U.S. Pat. No. 9,228,026 discloses further methods for the conjugation of vcMMAE to hLIV22.

Assays

MCF-7 (breast carcinoma) cells were obtained from ATCC. One day prior to assay, the MCF-7 cells were plated at a density of 2000 cells per well in 96-well plates, in Earles' Minimum Essential Media supplemented with 10% fetal bovine serum and 0.01 μg/mL insulin.

The in vitro cytotoxicity assay was used to determine activity of each drug on MCF-7 cells. Briefly, cells were incubated with the indicated drugs at a titration of concentrations for 120 hours. Viability of each drug was measured using Cell-titer Glo (Promega, Wisconsin) (FIG. 1, top). In another assay, viability of SGN-LIV1A (hLIV22-vcMMAE) was also measured using Cell-titer Glo (FIG. 1, bottom).

Combinations of SGN-LIV1A and one of the agents docetaxel, paclitaxel, doxorubicin, gemcitabine, NVP-BEZ235, everolimus, or cyclophosphamide were added to cells the following day and kept in a 5% $CO_2$ incubator at 37° C. for 120 hours. Cells were then lysed with Cell Titer Glo (Promega; Seattle, Wash.) for 60 minutes before viability was determined on an Envision plate reader (PerkinElmer; Waltham, Mass.).

To evaluate combination indexes (CI), SGN-LIV1A, doxorubicin, gemecitabine, and paclitaxel were combined at their ED50 concentrations or 2 fold higher or lower concentrations to obtain a 10 points dataset. The CI value was determined using CalcuSyn software (Biosoft; Cambridge, UK), which performs multiple drug dose-effect calculations using the Median Effect methods described by Chou and Talalay. See Chou TC (2010). Drug combination studies and their synergy quantification were performed using the Chou-Talalay method. *Cancer Res* 70: 440-446. Table 1 illustrates the results below:

TABLE 1

SGN-LIV1A Combinations

| Drug/Combination | ED50 | ED75 | ED90 | R values | Results |
|---|---|---|---|---|---|
| SGN-LIV1A | | | | 0.89 | |
| Doxorubicin | | | | 0.85 | |
| SGN-LIV1A + Doxorubicin | 0.78 | 0.95 | 1.15 | 0.85 | Moderate synergism to slight antagonism |
| Paclitaxel | | | | 0.82 | |
| SGN-LIV1A + Paclitaxel | 0.23 | 3.22 | 51.78 | 0.82 | Strong synergism to very strong antagonism |
| Gemcitabine | | | | 0.81 | |
| SGN-LIV1A + Gemcitabine | 0.73 | 2.57 | 9.18 | 0.84 | Moderate synergism to strong antagonism |
| SGN-LIV1A + Everolimus | 0.58 | 0.56 | 0.55 | 0.96 | Synergism |

Figure 2:
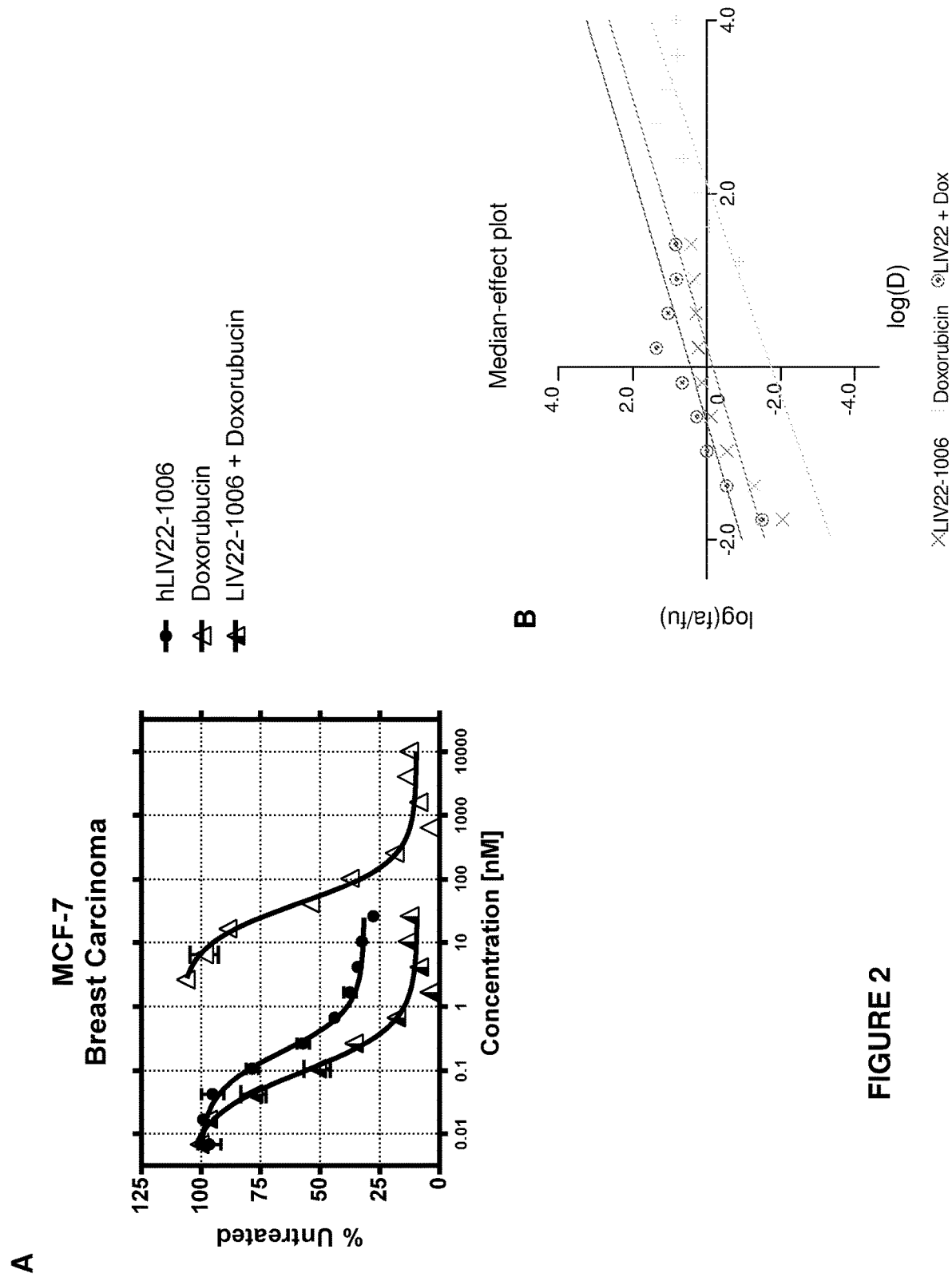
FIG. 2 shows the effect of SGN-LIV1A and doxorubicin on MCF-7 cells, according to an embodiment of the invention.
Figure 3:
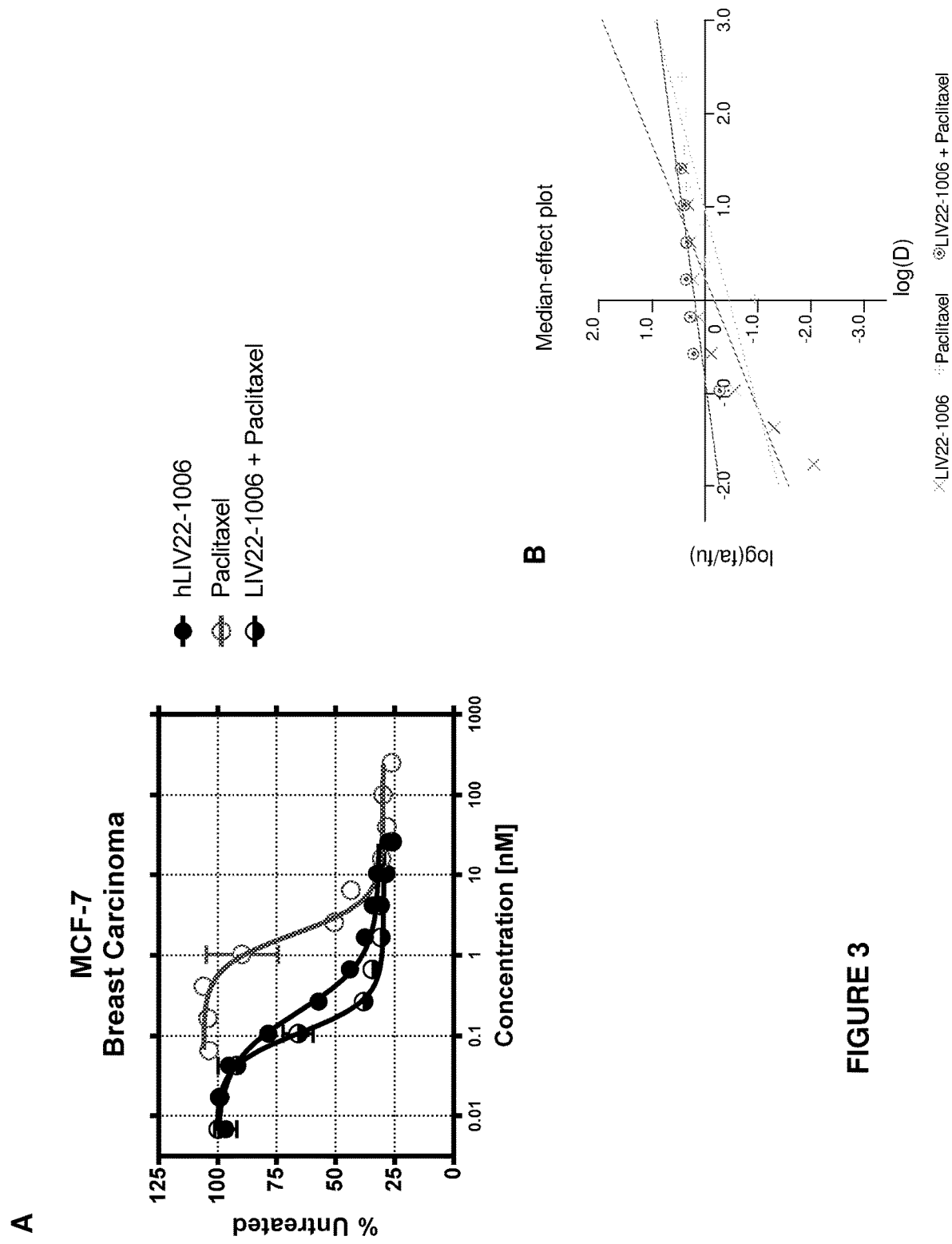
FIG. 3 shows the effect of SGN-LIV1A and paclitaxel on MCF-7 cells, according to an embodiment of the invention.
Figure 4:
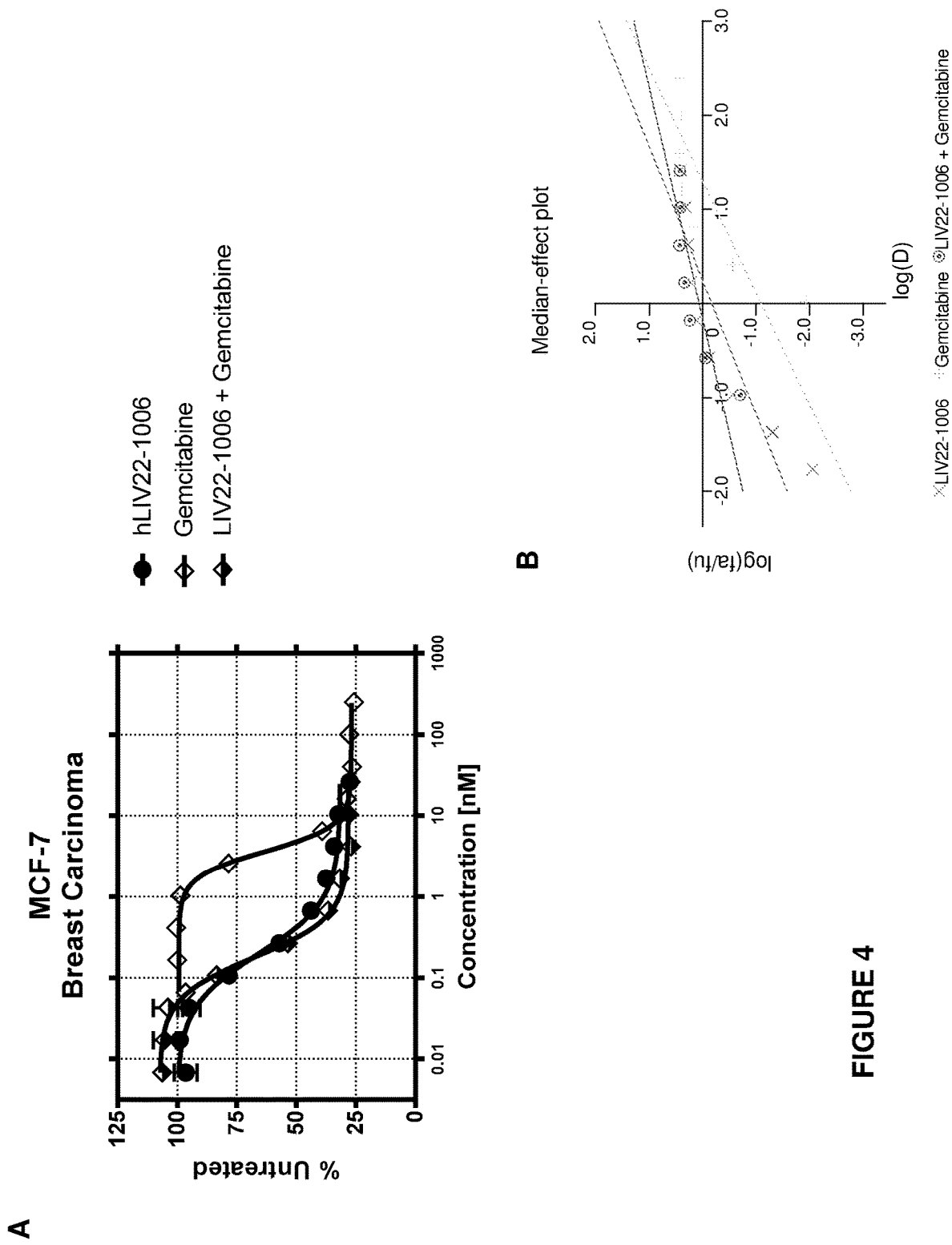
FIG. 4 shows the effect of SGN-LIV1A and gemcitabine on MCF-7 cells, according to an embodiment of the invention.
Figure 5:
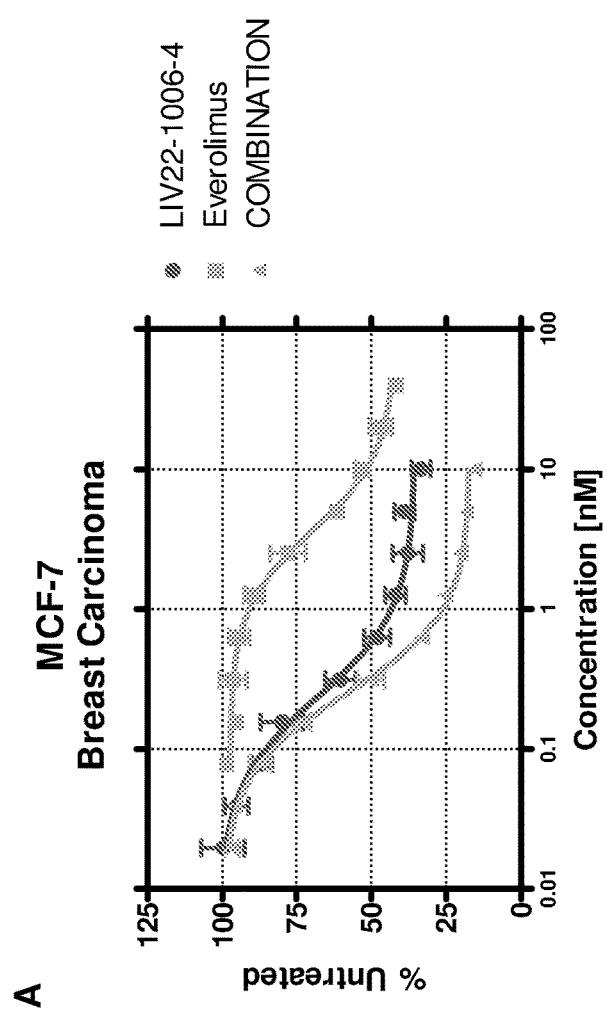
FIG. 5 shows the effect of SGN-LIV1A and everolimus on MCF-7 cells, according to an embodiment of the invention.
Figure 5:
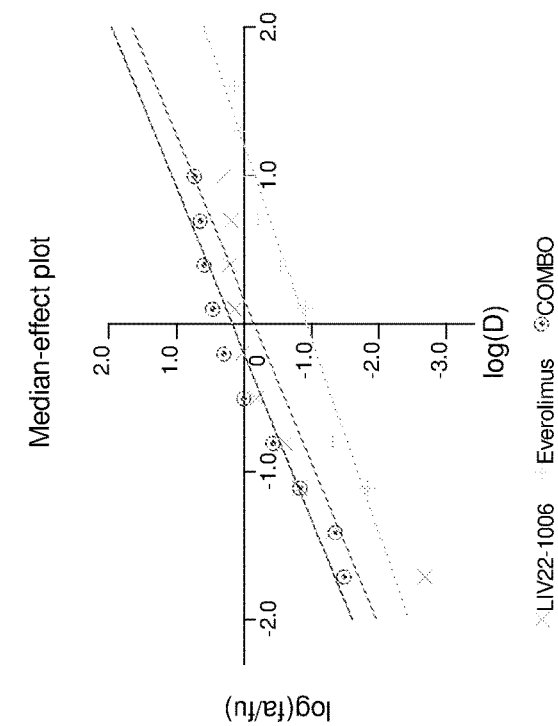

Table 1 and FIG. 2 show that SGN-LIV1A and doxorubicin were moderately synergistic at their respective ED50 and ED75 concentrations (CI<1), and slightly antagonistic at their ED 90 concentrations. Table 1 and FIG. 3 show that SGN-LIV1A and paclitaxel were strongly synergistic at the ED50 concentration, but antagonistic at ED75 or ED90. Table 1 and FIG. 4 show that SGN-LIV1A and gemcitabine were synergistic at the ED50 concentration, but not at the ED75 or ED90 concentrations. Table 1 and FIG. 5 show that SGN-LIV1A and everolimus were synergistic at the ED50, ED75, and ED90 concentrations.

II. In Vivo Assays

NOD Scid Gamma (NSG) mice were obtained from Jackson Laboratory and implanted with 17-β-estradiol pellet (Innovative Research of America; Sarasota, Fla.) one day prior to cell implant. Five million MCF-7 cells were implanted subcutaneously with Matrigel (BD Biosciences; Franklin Lakes, N.J.) and tumor volume was determined by a digital caliper twice a week, using the formula: volume=½×length width².

Figure 6:
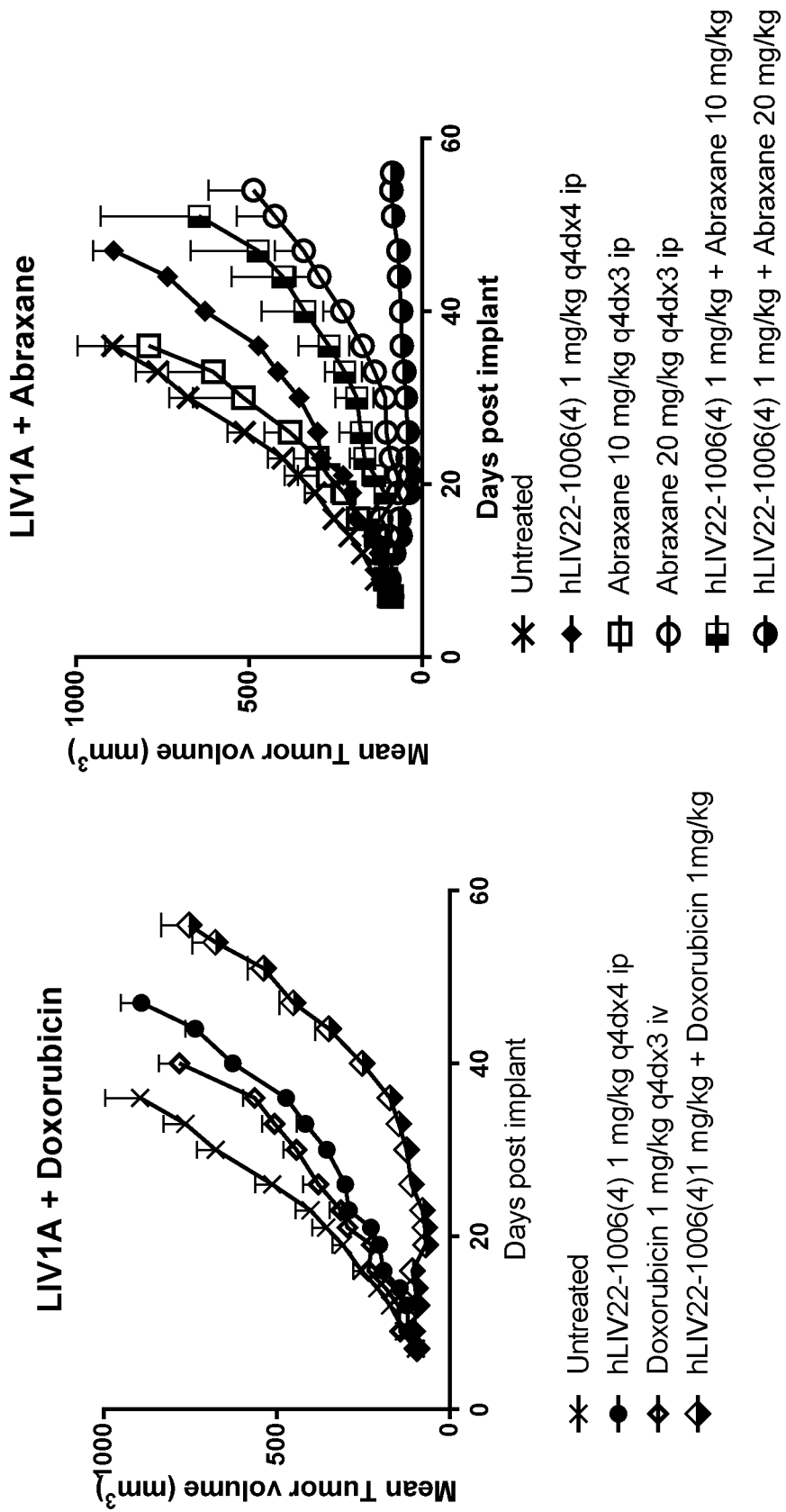
FIG. 6 shows the effects of SGN-LIV1A and either doxorubicin (left) or Abraxane (nab-paclitaxel) (right) on tumor growth in NOD Scid Gamma (NSG) mice, according to an embodiment of the invention.
Figure 7:
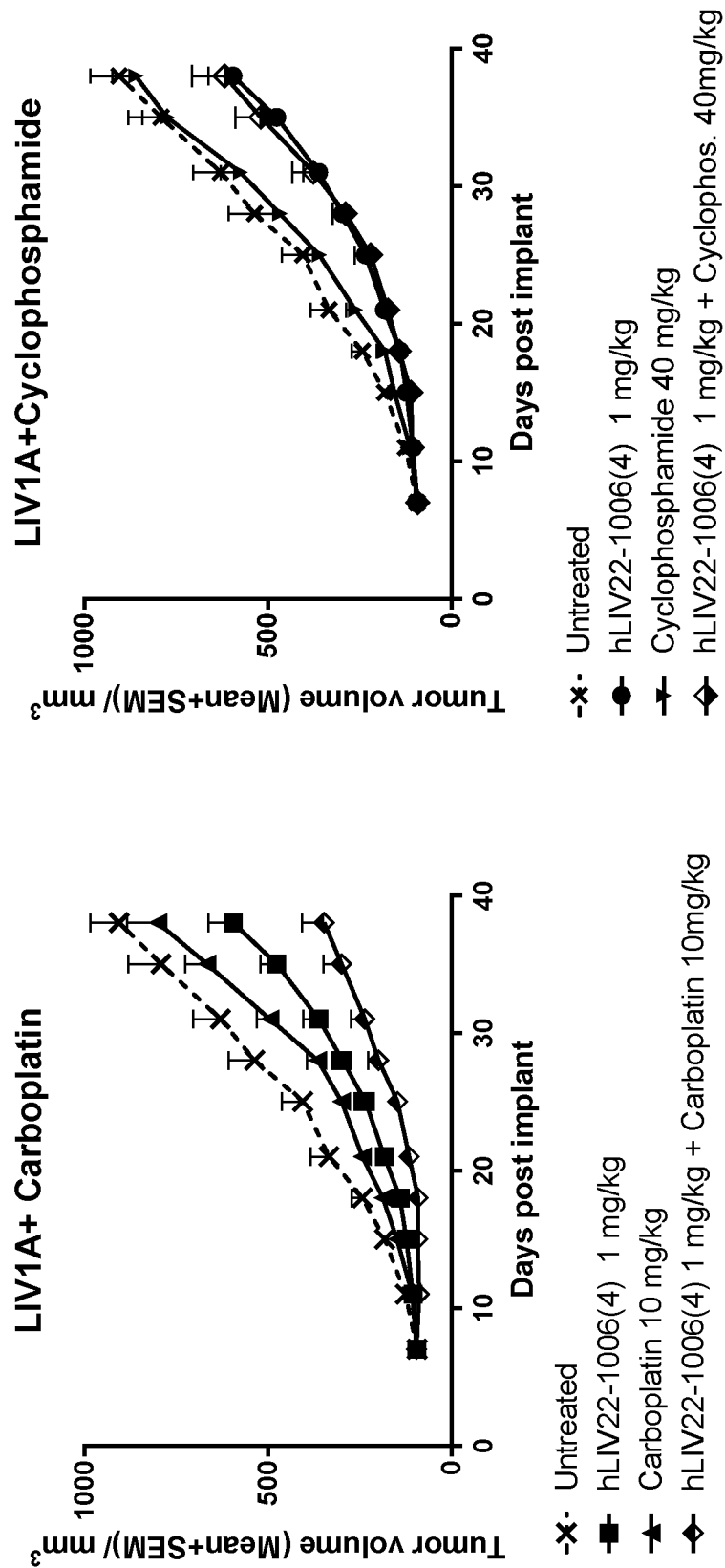
FIG. 7 shows the effects of SGN-LIV1A and either carboplatin (left) or cyclophosphamide (right) on tumor growth in NOD Scid Gamma (NSG) mice, according to an embodiment of the invention.
Figure 8:
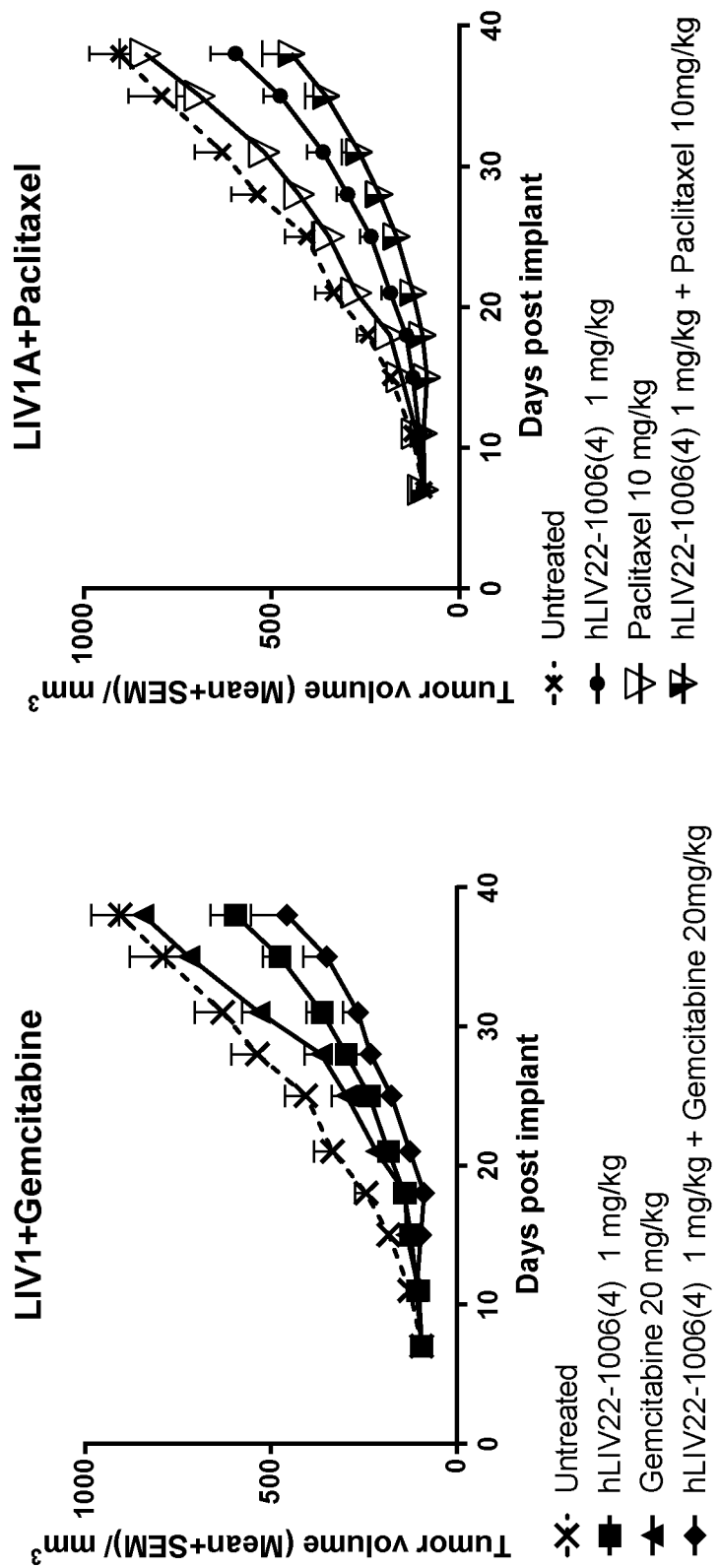
FIG. 8 shows the effects of SGN-LIV1A and either gemcitabine (left) or paclitaxel (right) on tumor growth in NOD Scid Gamma (NSG) mice, according to an embodiment of the invention.

Mice received treatments when the average tumor volume reached 100 mm³. The treatment regimen for each agent was: doxorubicin, 1 mg/kg q4dx3 intravenous (IV); SGN-LIV1, 1 mg/kg q4dx4 intraperitoneal (IP); nab-paclitaxel (nanoparticle albumin-bound paclitaxel) 20 mg/kg q4dx3 IP; carboplatin 10 mg/kg q7dx3 IP; cyclophosphamide, 40 mg/kg q7dx3 IV; gemcitabine 20 mg/kg q7dx2 IP; and paclitaxel 10 mg/kg q3dx5 IP. Combination groups received the first dose of SGN-LIV1A and combination drug on the same day. n=6 for each group. The effects of each drug and their combination on tumor growth were plotted in FIGS. 6-8.

To determine the combined benefit in vivo, tumor growth inhibition (TGI) was compared using the area under the curve between untreated, single agent groups, and combined groups on the date the untreated animals were euthanized (Table 2). The following formula was used to calculate the TGI: $TGI=1-AUC_{drugx}/AUC_{untreated}$. Thus, the expected additive TGI for combination is $(1-TGI_{drug\ x})\times(1-TGI_{drug\ y})$. When the TGI for the combination group is 10% greater than the expected TGI, the combination regimen is considered synergistic in vivo. The data in Table 2 shows that doxorubicin, 10 mg/kg nab-paclitaxel, and carboplatin provide the highest combinatorial benefit. Furthermore, the 20 mg/kg gemcitabine and 20 mg/kg nab-paclitaxel were found to be nearly additive when combined with SGN-LIV1A.

TABLE 2

Summary of In Vivo Tumor Growth Inhibition (TGI)

| Dose | | TGI | Expected combination TGI | Observed combination TGI | Combinatorial benefit |
|---|---|---|---|---|---|
| 1 mg/kg | SGN-LIV1A | 39% | | | |
| 1 mg/kg | doxorubicin | 26% | 55% | 75% | 20% |
| 20 mg/kg | nab-paclitaxel | 75% | 85% | 87% | 2% |
| 10 mg/kg | nab-paclitaxel | 23% | 53% | 62% | 9% |
| 10 mg/kg | carboplatin | 21% | 52% | 60% | 8% |
| 40 mg/kg | cyclophosphamide | 10% | 45% | 39% | -6% |
| 20 mg/kg | gemcitabine | 20% | 51% | 54% | 3% |

What is claimed is:

1. A method for treating a subject having cancer, the method comprising administering to the subject a LIV-1 antibody drug conjugate (LIV-1-ADC) and a checkpoint inhibitor, wherein the LIV-1-ADC comprises a humanized hLIV22 antibody conjugated to a vcMMAE (valine-citrulline-monomethyl auristatin E.

2. The method of claim 1, wherein the subject has breast cancer.

3. The method of claim 2, wherein the breast cancer is triple negative breast cancer, triple positive breast cancer, HER2-positive breast cancer, or hormone receptor positive cancer.

4. The method of claim 3, wherein the subject has triple negative breast cancer.

5. The method of claim 1, wherein the subject has prostate cancer, ovarian cancer, endometrial cancer, pancreatic cancer, lung cancer, a cervical cancer, a melanoma, or squamous cell carcinoma.

6. The method of claim 1, wherein the LIV-1-ADC is administered at a dosage between 1.5 mg/kg and 4 mg/kg of the subject's body weight.

7. The method of claim 1, wherein the LIV-1-ADC is administered at a dosage of 2.5 mg/kg of the subject's body weight.

8. The method of claim 1, wherein the LIV-1-ADC is administered once every 3 weeks.

9. The method of claim 1, wherein the LIV-1-ADC is administered by intravenous injection.

10. The method of claim 1, wherein the checkpoint inhibitor is an anti-PD-1 antibody, an anti-PD-L1 antibody, an anti-CTLA4 antibody, B7-DC-Fc, LAG3, or TIM3.

11. The method of claim 10, wherein the checkpoint inhibitor is an anti-PD-1 antibody.

12. The method of claim 11, wherein the anti-PD-1 antibody is MEDI0680, AMP-224, nivolumab, pembrolizumab, or pidilizumab.

* * * * *

SEQUENCE LISTING

<160> NUMBER OF SEQ ID NOS: 4

<210> SEQ ID NO 1
<211> LENGTH: 755
<212> TYPE: PRT
<213> ORGANISM: Homo sapiens

<400> SEQUENCE: 1

-continued

```
Met Ala Arg Lys Leu Ser Val Ile Leu Ile Leu Thr Phe Ala Leu Ser
1               5                   10                  15

Val Thr Asn Pro Leu His Glu Leu Lys Ala Ala Ala Phe Pro Gln Thr
            20                  25                  30

Thr Glu Lys Ile Ser Pro Asn Trp Glu Ser Gly Ile Asn Val Asp Leu
        35                  40                  45

Ala Ile Ser Thr Arg Gln Tyr His Leu Gln Gln Leu Phe Tyr Arg Tyr
    50                  55                  60

Gly Glu Asn Asn Ser Leu Ser Val Glu Gly Phe Arg Lys Leu Leu Gln
65                  70                  75                  80

Asn Ile Gly Ile Asp Lys Ile Lys Arg Ile His Ile His His Asp His
                85                  90                  95

Asp His His Ser Asp His Glu His His Ser Asp His Glu Arg His Ser
            100                 105                 110

Asp His Glu His His Ser Glu His Glu His His Ser Asp His Asp His
        115                 120                 125

His Ser His His Asn His Ala Ala Ser Gly Lys Asn Lys Arg Lys Ala
    130                 135                 140

Leu Cys Pro Asp His Asp Ser Asp Ser Ser Gly Lys Asp Pro Arg Asn
145                 150                 155                 160

Ser Gln Gly Lys Gly Ala His Arg Pro Glu His Ala Ser Gly Arg Arg
                165                 170                 175

Asn Val Lys Asp Ser Val Ser Ala Ser Glu Val Thr Ser Thr Val Tyr
            180                 185                 190

Asn Thr Val Ser Glu Gly Thr His Phe Leu Glu Thr Ile Glu Thr Pro
        195                 200                 205

Arg Pro Gly Lys Leu Phe Pro Lys Asp Val Ser Ser Thr Pro Pro
    210                 215                 220

Ser Val Thr Ser Lys Ser Arg Val Ser Arg Leu Ala Gly Arg Lys Thr
225                 230                 235                 240

Asn Glu Ser Val Ser Glu Pro Arg Lys Gly Phe Met Tyr Ser Arg Asn
                245                 250                 255

Thr Asn Glu Asn Pro Gln Glu Cys Phe Asn Ala Ser Lys Leu Leu Thr
            260                 265                 270

Ser His Gly Met Gly Ile Gln Val Pro Leu Asn Ala Thr Glu Phe Asn
        275                 280                 285

Tyr Leu Cys Pro Ala Ile Ile Asn Gln Ile Asp Ala Arg Ser Cys Leu
    290                 295                 300

Ile His Thr Ser Glu Lys Lys Ala Glu Ile Pro Pro Lys Thr Tyr Ser
305                 310                 315                 320

Leu Gln Ile Ala Trp Val Gly Phe Ile Ala Ile Ser Ile Ile Ser
                325                 330                 335

Phe Leu Ser Leu Leu Gly Val Ile Leu Val Pro Leu Met Asn Arg Val
            340                 345                 350

Phe Phe Lys Phe Leu Leu Ser Phe Leu Val Ala Leu Ala Val Gly Thr
        355                 360                 365

Leu Ser Gly Asp Ala Phe Leu His Leu Leu Pro His Ser His Ala Ser
    370                 375                 380

His His His Ser His Ser His Glu Glu Pro Ala Met Glu Met Lys Arg
385                 390                 395                 400

Gly Pro Leu Phe Ser His Leu Ser Ser Gln Asn Ile Glu Glu Ser Ala
                405                 410                 415

Tyr Phe Asp Ser Thr Trp Lys Gly Leu Thr Ala Leu Gly Gly Leu Tyr
```

```
                420             425             430
Phe Met Phe Leu Val Glu His Val Leu Thr Leu Ile Lys Gln Phe Lys
        435                 440                 445
Asp Lys Lys Lys Asn Gln Lys Lys Pro Glu Asn Asp Asp Asp Val
    450                 455                 460
Glu Ile Lys Lys Gln Leu Ser Lys Tyr Glu Ser Gln Leu Ser Thr Asn
465                 470                 475                 480
Glu Glu Lys Val Asp Thr Asp Arg Thr Glu Gly Tyr Leu Arg Ala
                485                 490                 495
Asp Ser Gln Glu Pro Ser His Phe Asp Ser Gln Gln Pro Ala Val Leu
            500                 505                 510
Glu Glu Glu Glu Val Met Ile Ala His Ala His Pro Gln Glu Val Tyr
            515                 520                 525
Asn Glu Tyr Val Pro Arg Gly Cys Lys Asn Lys Cys His Ser His Phe
        530                 535                 540
His Asp Thr Leu Gly Gln Ser Asp Asp Leu Ile His His His Asp
545                 550                 555                 560
Tyr His His Ile Leu His His His His Gln Asn His His Pro His
                565                 570                 575
Ser His Ser Gln Arg Tyr Ser Arg Glu Leu Lys Asp Ala Gly Val
            580                 585                 590
Ala Thr Leu Ala Trp Met Val Ile Met Gly Asp Gly Leu His Asn Phe
            595                 600                 605
Ser Asp Gly Leu Ala Ile Gly Ala Ala Phe Thr Glu Gly Leu Ser Ser
        610                 615                 620
Gly Leu Ser Thr Ser Val Ala Val Phe Cys His Glu Leu Pro His Glu
625                 630                 635                 640
Leu Gly Asp Phe Ala Val Leu Leu Lys Ala Gly Met Thr Val Lys Gln
                645                 650                 655
Ala Val Leu Tyr Asn Ala Leu Ser Ala Met Leu Ala Tyr Leu Gly Met
                660                 665                 670
Ala Thr Gly Ile Phe Ile Gly His Tyr Ala Glu Asn Val Ser Met Trp
            675                 680                 685
Ile Phe Ala Leu Thr Ala Gly Leu Phe Met Tyr Val Ala Leu Val Asp
            690                 695                 700
Met Val Pro Glu Met Leu His Asn Asp Ala Ser Asp His Gly Cys Ser
705                 710                 715                 720
Arg Trp Gly Tyr Phe Phe Leu Gln Asn Ala Gly Met Leu Leu Gly Phe
                725                 730                 735
Gly Ile Met Leu Leu Ile Ser Ile Phe Glu His Lys Ile Val Phe Arg
            740                 745                 750
Ile Asn Phe
        755

<210> SEQ ID NO 2
<211> LENGTH: 749
<212> TYPE: PRT
<213> ORGANISM: Homo sapiens

<400> SEQUENCE: 2

Met Ala Arg Lys Leu Ser Val Ile Leu Ile Leu Thr Phe Ala Leu Ser
1               5                   10                  15
Val Thr Asn Pro Leu His Glu Leu Lys Ala Ala Ala Phe Pro Gln Thr
            20                  25                  30
```

```
Thr Glu Lys Ile Ser Pro Asn Trp Glu Ser Gly Ile Asn Val Asp Leu
         35                  40                  45

Ala Ile Ser Thr Arg Gln Tyr His Leu Gln Gln Leu Phe Tyr Arg Tyr
 50                  55                  60

Gly Glu Asn Asn Ser Leu Ser Val Glu Gly Phe Arg Lys Leu Leu Gln
 65                  70                  75                  80

Asn Ile Gly Ile Asp Lys Ile Lys Arg Ile His Ile His His Asp His
                 85                  90                  95

Asp His His Ser Asp His Glu His Ser Asp His Glu Arg His Ser
            100                 105                 110

Asp His Glu His His Ser Asp His Glu His His Ser Asp His Asn His
        115                 120                 125

Ala Ala Ser Gly Lys Asn Lys Arg Lys Ala Leu Cys Pro Asp His Asp
    130                 135                 140

Ser Asp Ser Ser Gly Lys Asp Pro Arg Asn Ser Gln Gly Lys Gly Ala
145                 150                 155                 160

His Arg Pro Glu His Ala Ser Gly Arg Arg Asn Val Lys Asp Ser Val
                165                 170                 175

Ser Ala Ser Glu Val Thr Ser Thr Val Tyr Asn Thr Val Ser Glu Gly
            180                 185                 190

Thr His Phe Leu Glu Thr Ile Glu Thr Pro Arg Pro Gly Lys Leu Phe
        195                 200                 205

Pro Lys Asp Val Ser Ser Ser Thr Pro Pro Ser Val Thr Ser Lys Ser
    210                 215                 220

Arg Val Ser Arg Leu Ala Gly Arg Lys Thr Asn Glu Ser Val Ser Glu
225                 230                 235                 240

Pro Arg Lys Gly Phe Met Tyr Ser Arg Asn Thr Asn Glu Asn Pro Gln
                245                 250                 255

Glu Cys Phe Asn Ala Ser Lys Leu Leu Thr Ser His Gly Met Gly Ile
            260                 265                 270

Gln Val Pro Leu Asn Ala Thr Glu Phe Asn Tyr Leu Cys Pro Ala Ile
        275                 280                 285

Ile Asn Gln Ile Asp Ala Arg Ser Cys Leu Ile His Thr Ser Glu Lys
    290                 295                 300

Lys Ala Glu Ile Pro Pro Lys Thr Tyr Ser Leu Gln Ile Ala Trp Val
305                 310                 315                 320

Gly Gly Phe Ile Ala Ile Ser Ile Ile Ser Phe Leu Ser Leu Leu Gly
                325                 330                 335

Val Ile Leu Val Pro Leu Met Asn Arg Val Phe Phe Lys Phe Leu Leu
            340                 345                 350

Ser Phe Leu Val Ala Leu Ala Val Gly Thr Leu Ser Gly Asp Ala Phe
        355                 360                 365

Leu His Leu Leu Pro His Ser His Ala Ser His His Ser His Ser
    370                 375                 380

His Glu Glu Pro Ala Met Glu Met Lys Arg Gly Pro Leu Phe Ser His
385                 390                 395                 400

Leu Ser Ser Gln Asn Ile Glu Glu Ser Ala Tyr Phe Asp Ser Thr Trp
                405                 410                 415

Lys Gly Leu Thr Ala Leu Gly Gly Leu Tyr Phe Met Phe Leu Val Glu
            420                 425                 430

His Val Leu Thr Leu Ile Lys Gln Phe Lys Asp Lys Lys Lys Lys Asn
        435                 440                 445

Gln Lys Lys Pro Glu Asn Asp Asp Asp Val Glu Ile Lys Lys Gln Leu
```

```
                450             455             460
Ser Lys Tyr Glu Ser Gln Leu Ser Thr Asn Glu Glu Lys Val Asp Thr
465                 470                 475                 480

Asp Asp Arg Thr Glu Gly Tyr Leu Arg Ala Asp Ser Gln Glu Pro Ser
                485                 490                 495

His Phe Asp Ser Gln Gln Pro Ala Val Leu Glu Glu Glu Val Met
                500                 505                 510

Ile Ala His Ala His Pro Gln Glu Val Tyr Asn Glu Tyr Val Pro Arg
                515                 520                 525

Gly Cys Lys Asn Lys Cys His Ser His Phe His Asp Thr Leu Gly Gln
                530                 535                 540

Ser Asp Asp Leu Ile His His His Asp Tyr His His Ile Leu His
545                 550                 555                 560

His His His His Gln Asn His His Pro His Ser His Ser Gln Arg Tyr
                565                 570                 575

Ser Arg Glu Glu Leu Lys Asp Ala Gly Val Ala Thr Leu Ala Trp Met
                580                 585                 590

Val Ile Met Gly Asp Gly Leu His Asn Phe Ser Asp Gly Leu Ala Ile
                595                 600                 605

Gly Ala Ala Phe Thr Glu Gly Leu Ser Ser Gly Leu Ser Thr Ser Val
                610                 615                 620

Ala Val Phe Cys His Glu Leu Pro His Glu Leu Gly Asp Phe Ala Val
625                 630                 635                 640

Leu Leu Lys Ala Gly Met Thr Val Lys Gln Ala Val Leu Tyr Asn Ala
                645                 650                 655

Leu Ser Ala Met Leu Ala Tyr Leu Gly Met Ala Thr Gly Ile Phe Ile
                660                 665                 670

Gly His Tyr Ala Glu Asn Val Ser Met Trp Ile Phe Ala Leu Thr Ala
                675                 680                 685

Gly Leu Phe Met Tyr Val Ala Leu Val Asp Met Val Pro Glu Met Leu
                690                 695                 700

His Asn Asp Ala Ser Asp His Gly Cys Ser Arg Trp Gly Tyr Phe Phe
705                 710                 715                 720

Leu Gln Asn Ala Gly Met Leu Leu Gly Phe Gly Ile Met Leu Leu Ile
                725                 730                 735

Ser Ile Phe Glu His Lys Ile Val Phe Arg Ile Asn Phe
                740                 745

<210> SEQ ID NO 3
<211> LENGTH: 113
<212> TYPE: PRT
<213> ORGANISM: Artificial Sequence
<220> FEATURE:
<223> OTHER INFORMATION: Light chain variable region of hLIV22

<400> SEQUENCE: 3

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
                20                  25                  30

Ser Gly Asn Thr Tyr Leu Glu Trp Tyr Gln Gln Arg Pro Gly Gln Ser
                35                  40                  45

Pro Arg Pro Leu Ile Tyr Lys Ile Ser Thr Arg Phe Ser Gly Val Pro
            50                  55                  60

Asp Arg Phe Ser Gly Ser Gly Ser Gly Thr Asp Phe Thr Leu Lys Ile
```

-continued

```
                65                  70                  75                  80
Ser Arg Val Glu Ala Glu Asp Val Gly Val Tyr Tyr Cys Phe Gln Gly
                    85                  90                  95
Ser His Val Pro Tyr Thr Phe Gly Gly Gly Thr Lys Val Glu Ile Lys
                100                 105                 110
Arg

<210> SEQ ID NO 4
<211> LENGTH: 120
<212> TYPE: PRT
<213> ORGANISM: Artificial Sequence
<220> FEATURE:
<223> OTHER INFORMATION: Heavy chain variable region of hLIV22

<400> SEQUENCE: 4

Gln Val Gln Leu Val Gln Ser Gly Ala Glu Val Lys Lys Pro Gly Ala
1               5                   10                  15
Ser Val Lys Val Ser Cys Lys Ala Ser Gly Leu Thr Ile Glu Asp Tyr
                20                  25                  30
Tyr Met His Trp Val Arg Gln Ala Pro Gly Gln Gly Leu Glu Trp Met
            35                  40                  45
Gly Trp Ile Asp Pro Glu Asn Gly Asp Thr Glu Tyr Gly Pro Lys Phe
        50                  55                  60
Gln Gly Arg Val Thr Met Thr Arg Asp Thr Ser Ile Asn Thr Ala Tyr
65                  70                  75                  80
Met Glu Leu Ser Arg Leu Arg Ser Asp Asp Thr Ala Val Tyr Tyr Cys
                85                  90                  95
Ala Val His Asn Ala His Tyr Gly Thr Trp Phe Ala Tyr Trp Gly Gln
                100                 105                 110
Gly Thr Leu Val Thr Val Ser Ser
            115                 120
```